US012582558B2

(12) United States Patent
Deelen

(10) Patent No.: US 12,582,558 B2
(45) Date of Patent: Mar. 24, 2026

(54) APPARATUS FOR MANUFACTURING AN ABSORBENT CORE, A PARTICLE REDIRECTOR AND A METHOD OF REDIRECTING PARTICLES

(71) Applicant: Essity Hygiene and Health Aktiebolag, Gothenburg (SE)

(72) Inventor: Bert Deelen, KN Gieten (NL)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 155 days.

(21) Appl. No.: 18/698,115

(22) PCT Filed: Dec. 15, 2021

(86) PCT No.: PCT/EP2021/085945
§ 371 (c)(1),
(2) Date: Apr. 3, 2024

(87) PCT Pub. No.: WO2023/110085
PCT Pub. Date: Jun. 22, 2023

(65) Prior Publication Data
US 2024/0398631 A1 Dec. 5, 2024

(51) Int. Cl.
*A61F 13/15* (2006.01)
*D04H 1/04* (2012.01)
*D04H 1/736* (2012.01)

(52) U.S. Cl.
CPC ......... *A61F 13/15642* (2013.01); *D04H 1/04* (2013.01); *D04H 1/736* (2013.01); *D10B 2509/026* (2013.01)

(58) Field of Classification Search
CPC .......... D04H 1/736; D04H 1/04; B05C 19/04; A61F 13/15617; A61F 13/15642; A61F 13/15658; D10B 2509/026
See application file for complete search history.

(56) References Cited

U.S. PATENT DOCUMENTS

| | | | |
|---|---|---|---|
| 5,447,677 A | 9/1995 | Griffoul et al. | |
| 5,558,832 A | 9/1996 | Noel et al. | |

(Continued)

FOREIGN PATENT DOCUMENTS

| | | |
|---|---|---|
| CN | 108852625 A | 11/2018 |
| CN | 110575313 A | 12/2019 |
| CN | 110575314 A | 12/2019 |

(Continued)

OTHER PUBLICATIONS

International Search Report (PCT/ISA/210) and Written Opinion (PCT/ISA/237) mailed on Sep. 1, 2022, by the European Patent Office as the International Searching Authority for International Application No. PCT/EP2021/085945, 12 pages.

(Continued)

*Primary Examiner* — Monica A Huson
(74) *Attorney, Agent, or Firm* — BUCHANAN INGERSOLL & ROONEY PC

(57) ABSTRACT

The present disclosure relates to an apparatus for manufacturing an absorbent core for an absorbent product, said absorbent core includes a fibrous material and particles dispersed throughout at least a portion of said fibrous material. The disclosure also relates to a particle redirector and a method of redirecting particles.

31 Claims, 17 Drawing Sheets

(56)         References Cited

U.S. PATENT DOCUMENTS

| | | |
|---|---|---|
| 8,960,122 B2 | 2/2015 | Yano et al. |
| 9,107,779 B2 | 8/2015 | Mukai et al. |

FOREIGN PATENT DOCUMENTS

| | | | | |
|---|---|---|---|---|
| EP | 1023884 A2 | 8/2000 | | |
| EP | 1053729 A1 | 11/2000 | | |
| EP | 2915513 A1 | 9/2015 | | |
| EP | 3278778 A1 * | 2/2018 | ....... | A61F 13/15658 |
| JP | 4312112 B2 | 5/2009 | | |
| JP | 4711946 B2 | 4/2011 | | |
| JP | 5006562 B2 | 6/2012 | | |
| JP | 2018105760 A | 7/2018 | | |
| WO | 2010013736 A1 | 2/2010 | | |
| WO | 2012090508 A1 | 7/2012 | | |
| WO | 2014125978 A1 | 8/2014 | | |
| WO | 2015087674 A1 | 6/2015 | | |

OTHER PUBLICATIONS

Notice of Reasons for Refusal issued in Japanese Patent Application No. 2024-535996, dated Jan. 20, 2026, with English Translation (17 pages).

* cited by examiner

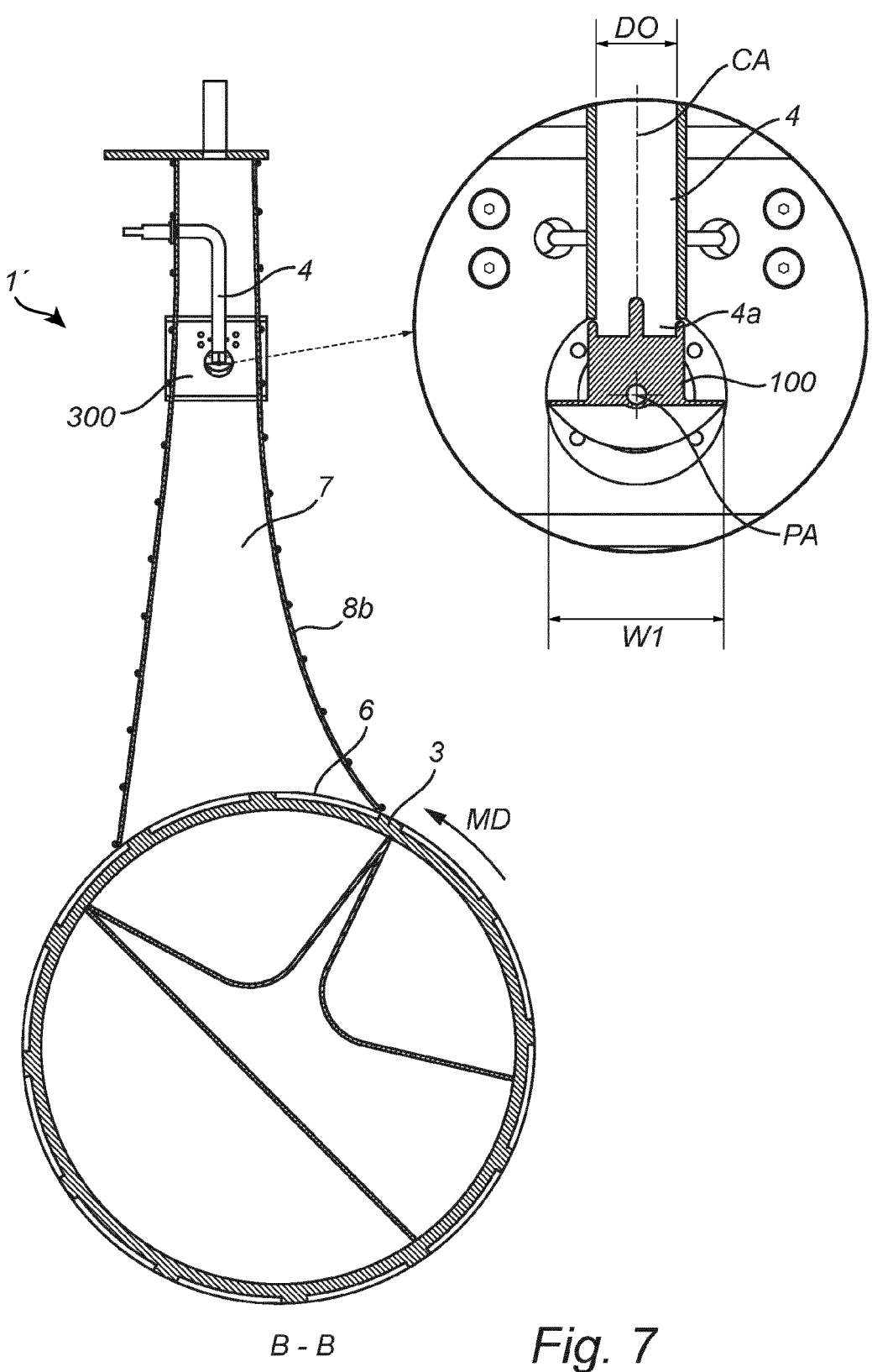
B - B          *Fig. 7*

APPARATUS FOR MANUFACTURING AN ABSORBENT CORE, A PARTICLE REDIRECTOR AND A METHOD OF REDIRECTING PARTICLES

TECHNICAL FIELD

This disclosure relates to an apparatus for manufacturing an absorbent core for an absorbent product. The disclosure also relates to a particle redirector and a method of redirecting particles.

BACKGROUND

Absorbent products, such as diapers, training pants, napkins, incontinence pads and the like, contain an absorbent core usually comprising a soft, fluffy material, such as comminuted wood pulp fibers. Various secondary materials are often incorporated into the absorbent fluff material, such as particles of super absorbent polymers (SAP), heat activatable bonding fibers or odour absorbent material. Super absorbent materials, also called super absorbent particles are polymers having the ability to absorb water and bodily fluids many times their own weight. The super absorbent material is either mixed with the fluff pulp fibers or applied in a layered configuration between layers of fluff pulp.

One way to produce such an absorbent core containing super absorbent polymers is to form a first layer of absorbent fluff pulp, whereupon the super absorbent polymers are sprinkled on top of the fluff pulp. A second layer of absorbent fluff pulp is then placed on top of the second material to complete the core. The absorbent core may further comprise two or more layers of super absorbent polymers disposed between layers of absorbent fluff pulp fibers. A result of this method is that it produces a product with a layered configuration, in which the super absorbent polymers are concentrated in fairly discrete zones within the core.

Alternatively, the SAP particles are mixed with and distributed throughout the first material (the absorbent fluff pulp fibers). It is further known to make absorbent products including a first and a second layer, in which the first layer contains a pure first material and the second layer contains a mixture of the first and the second material.

One way to produce an absorbent core for products with a fairly uniform distribution of the second material within the core is disclosed in patent document U.S. Pat. No. 5,447,677. In said disclosure there is presented an apparatus for making absorbent products containing a first material, such as absorbent fluff from wood pulp fibers. Said absorbent fluff pulp is introduced into a vacuum-forming chamber. A portion of the fluff pulp is deposited into the cavity of a mould transported through the forming chamber by a mat-forming wheel so as to form a layer of pure fluff pulp within the bottom of the mould cavity. A second material, such as superabsorbent particles or heat activatable bonding fibers, is introduced into the forming chamber so that streams of the first and second materials collide within a mixing zone. As the mould continues it travels through the forming chamber. A mixture of first and second materials from the mixing zone is deposited within the mould cavity, thereby filling it. The result is an absorbent core having a first layer formed by pure first material and a second layer formed by a mixture of the first and second materials.

A more detailed description of a known apparatus to manufacture an absorbent product of the design as discussed is made here by reference to FIG. 1. FIG. 1 shows an apparatus 1 and from a defibration unit pulp fibers are transported by the aid of air up to hoods 8a, 8b and through the hoods towards a mat-forming wheel 3. The mat-forming wheel 3 is provided with stationary suction boxes 2, wherein very low pressure prevails. The suction boxes face said hoods containing the pulp fibers. On the surface of the mat-forming wheel 3 an air pervious means, such as a net or a perforated plate, is provided. When said air pervious means rotates, in the direction shown by the arrow 3b, under said hoods the pulp fibers are forced by an air stream towards the air pervious means and form a core of pulp fibers along the circumference of the mat-forming wheel in the shape of a continuous mat. Said circumference may be provided with moulds for forming separate absorbent cores of different designs.

The core may further be formed into several layers by the use of several hoods. The core may, as stated, be formed into discrete cores or if a continuous mat-formed core is formed, it may be later cut into the desired design.

A flow of super absorbent particles (SAP) is added to the pulp fibers by an injection of the super absorbent particles through a pipe 4, i.e. a particle supply duct, into one or more of the hoods 8a, 8b. After the last hood (in the figure hood 8b) the core formation is completed and the core is kept in the mould or moulds on the wheel by means of an underpressure in a second stationary suction box 5. The core is, after the passage past said second suction box 5, transferred to a transfer drum 9, where it may be compressed, for example by means of a mechanical pressure exerted on the core during its passage over the transfer drum. Finally, the core is transferred to a conveyor 16 for further treatment or packaging. Transfer from the mat-forming wheel 3 to the conveyor 16 may be undertaken without the transfer drum.

An end product may consist of several cores, whereby the manufacturing assembly for said end product consists of two or more mat-forming wheels 3, each one of the wheels forming a core, whereupon the two or more resulting cores are assembled to the end product.

This way of manufacturing an absorbent core gives a core with an even layer of super absorbent particles throughout the mould.

There may however be cases when it is preferably to have super absorbent particles in specific areas in the mould to create a high absorbent zone within the core, for example in the front portion of the core or the rear portion.

EP1053729 A1 shows a method and apparatus for intermittently applying particulate material to a substrate with accurate placement within the substrate. However, there is need for an alternative solution.

SUMMARY

It is desired to provide an alternative system which can distribute particles to specific areas of an absorbent core and at the same time is a flexible system.

In accordance with a first aspect of the present disclosure, there is provided an apparatus for manufacturing an absorbent core for an absorbent product, said absorbent core comprises a fibrous material and particles dispersed throughout at least a portion of said fibrous material, said apparatus comprises a movable mat-forming device comprising at least one mould, said movable mat-forming device is movable in a machine direction;

a passage for directing at least a mixture of said fibrous material and said particles towards said at least one mould for depositing at least one layer of a mixture of said mixture of said fibrous material and said particles in said mould and a particle supply duct having an opening inside said passage.

The apparatus further comprises a particle redirector arranged adjacent to said opening of said particle supply duct and said particle redirector is pivotable in said machine direction or against said machine direction around a pivot axis extending in the cross direction to said machine direction and thereby redirecting said particles to at least one area on said at least one mould.

By having the particle redirector pivotable around a pivot axis adjacent the opening of the particle supply duct the particle redirector can redirect the particles from the particle supply duct to a at least one specific area on the mould. With adjacent it meant that the particle redirector is arranged in close proximity to the opening.

The area on the mould which shall receive the particles may be predefined. The area may also be redefined, i.e. it may change throughout the process of making the absorbent cores.

The mat-forming device may be a mat-forming wheel or a mat-forming belt. Both may be provided with a continuous mould extending along the circumference of the device. A continuous mould is utilized when the fibers deposited on the air pervious means are to be used to form a continuous layer, which is subsequently cut into suitable dimensions and shapes to form individual absorbent cores of an absorbent product. Alternatively, a series of separate moulds may be arranged along the circumference of the mat-forming device. Separate moulds are used to directly form cores of a special shape and dimension to form an absorbent core of an absorbent product. The mould or the moulds on the movable mat-forming device moves along the machine direction and during the movement of the mould the particle redirector may in a first step pivot either in the same direction as the movable mat-forming device or in the opposite direction. Depending on the pivot speed and the pivoting direction the particles can be steered to a specific area or to specific areas on the mould. When the mould has been filled with the particles in the specific area or areas the particle redirector can in a second step move in a direction opposite to the first step or in the same direction to a starting position so that the particle redirector is ready to fill a mould coming after the first mould if the mat-forming device is provided with a series of separate moulds. The particles can be distributed to the same area in all the moulds or they may differ from one mould to another. Alternatively, several moulds, for example ten moulds may be filled in the same area, and then the following ten moulds are filled with particles in a different area. The same applies if it is a continuous mould but then the particles are directed to different positions on the continuous mould so when the individual absorbent cores are cut they have the particle in their predetermined area.

The passage for directing at least a mixture of the fibrous material and the particles towards the moulds may be formed by a hood.

The opening of the particle supply duct is arranged at a distance from the movable mat-forming device such that the fibrous material and the particles can mix before they reach the mould. For example, the distance may be 100-200 cm, more preferably 130-170 cm. Hence, the redirected particles may be mixed the fibrous material before they are arranged in the mould.

In one example embodiment said particle redirector comprises a base which has convex surface and an opposite concave surface and a peripheral edge. A first imaginary plane is aligned along said pivot axis and bisects said base into two halves such that the cross section of said base taken along said first imaginary plane is U- or V-shaped. A second imaginary plane is perpendicular to said first imaginary plane and said first imaginary plane and said second imaginary plane intersect along said pivot axis. A third imaginary plane bisects said base into two halves. Said third imaginary plane is perpendicular to said first imaginary plane and said second imaginary plane and said third imaginary plane intersects with said first imaginary plane along a first axis and intersects with said second said imaginary plane along a second axis. Said particle redirector comprising at least a first flange and a second flange extending from said convex surface on respective sides of said first imaginary plane, and essentially parallel with the first imaginary plane, wherein said concave surface or said convex surface together with said flanges direct said particles towards said mould and said pivot axis is arranged at the centre of gravity of said particle redirector or at distance from said centre of gravity along said first imaginary plane.

Depending how the surfaces of the particle redirector, i.e. the concave surface or said convex surface together with said flanges are arranged in relation to the opening of the particle supply duct in a first position, i.e. a starting position, the particles can be directed to at least one area on the mould. By choosing a specific starting position of the particle redirector the area where the particles will be can be decided.

The pivot axis may be arranged in the centre of gravity of the particle redirector since it can then smoothly rotate. However, it will still work to have it a distance from the centre of gravity. An advantage of having the pivot axis in the centre of gravity is that the motor load will be lower than if it is arranged at a distance from the centre of gravity. The forces on the mechanical construction, for example bearings will also be lower if the pivot axis is arranged in the centre of gravity.

The base may have an overall oval shape. The base may also have an overall round shape or any suitable shape. The two flanges may be arranged at the same distance from the first imaginary plane.

In one example embodiment the first imaginary plane bisects said base into two equal halves and said third imaginary plane bisects said base into two equal halves. This way the particle redirector may be symmetric on each side of the first imaginary plane and the third imaginary plane.

In one example embodiment said particles are super absorbent particles, heat activatable bonding particles or odour absorbent particles.

In one example embodiment said fibrous material is a soft, fluffy material, such as comminuted wood pulp fibers.

In one example embodiment a third flange extends from said convex surface aligned and parallel with said first imaginary plane. The third flange is arranged between the first and the second flange and just as the first and the second flange it helps to direct the particles. The particle director is not limited to have two or three flanges it may have more, for example, four or five flanges. The flanges may have a round outer contour or a rectangular shape or any other suitable shape when viewed from the normal direction of said first imaginary plane.

In one example embodiment a fourth flange extends from said convex surface aligned and parallel with said third imaginary plane between said first and said second flange.

This fourth flange connects the first and the second flanges together, and also the third flange if there is a third flange between the first and second flange. The fourth flange may add stability to the particle redirector.

In one example embodiment said pivot axis at a cross-section taken along said third imaginary plane is arranged at a substantially equal predetermined distance from a highest point of each said first, second and/or third flange and from an outer point of the peripheral edge on each side of the first imaginary plane. Hence, the distance between the pivot axis and the highest point of the first flange is the same as the distance between the pivot axis and the second or third flange. The distance between the pivot axis and one of the outer points is the same as the distance between the pivot axis and the highest points of the flanges. That is, at the cross-section taken along the third imaginary plane a partial circle can be drawn from the first outer point of the peripheral edge, via the highest points of each flange to the second outer point of the peripheral edge on the opposite side of the first imaginary plane. The radius of the partial circle is the same as the predetermined distance.

In one example embodiment said first, second and/or third flange each has a curved outer shape extending from a highest point of each respective flange towards said convex surface, viewed from the normal direction of said first imaginary plane. The curved outer shape may be symmetrically on both sides of the third imaginary plane. By having a curved outer shape it is prevented that fibrous material is piled up on the flanges, which later may fall down and into the mould and create hard areas in the core.

In one example embodiment the particle redirector has an outer contour, formed by the first, second and/or third flanges together with the base which follows the shape of an imaginary surface of a partially imaginary ellipsoid.

In one example embodiment at least a part of said particle redirector protrude into said opening of the particle supply duct or said particle redirector is arranged in close proximity to said opening of said particle supply duct. This way it is accomplished that most of the particles from the particle supply duct hits the particle redirector in order to direct the particles toward the mould.

In one example embodiment there is a gap having a predetermined distance between the wall of the particle supply duct, i.e. the end of the particle supply duct and the first and second flanges and/or said third flanges when the particle redirector is pivoting and passing the particle supply duct. The predetermined distance is preferable minimized in order to reduce uncontrolled airflows into unwanted directions. The pre-determined distance may preferably be 1-4 mm, more preferably 2 mm In one example embodiment said opening of said particle supply duct has a shape and/or a diameter which allows said outer contour of said particle redirector to pivot freely adjacent or at least partly inside said particle supply duct.

In one example embodiment the first and the second flanges are arranged at a distance from each other which is equal, smaller or larger than the inner diameter opening of the particle supply duct. If the distance is equal or larger the particles will hit the convex surface between the flanges when the convex surface is arranged to face the opening of the particle supply duct. That is when the second plane is facing the opening of the particle supply duct. This is especially the case if parts of the flanges protrude into the opening. If the distance between the flanges is smaller some particles may hit the convex surface between the first flange and the peripheral edge and/or the convex surface between the second flange and the peripheral edge on the other side.

In one example embodiment the maximum width of the base of the particle redirector is at a cross section taken along said first imaginary plane is equal or larger than the inner diameter of the particle supply duct. This assures that most particle hit the base and can be directed by either the convex or concave side of the base.

In one example embodiment said first axis of said particle redirector is aligned with a centre axis of said particle supply duct. This way it is ensured that the particle director is aligned with the particle supply duct.

In one example embodiment said particle redirector comprises a shaft connecting element extending along said pivot axis adapted to house a shaft which is connectable to said shaft connecting element in order to pivot said particle redirector around said pivot axis.

In one example embodiment said particle redirector is pivotable around said pivot axis by a shaft connected to said particle redirector which is rotatable supported in said passage.

In one example embodiment the particle redirector is attached to a hood forming said passage.

In one example embodiment said particle redirector is pivotable around said pivot axis by a motor. The motor may be an AC-servo motor. The motor can be steered by a programmable position control system in, for example, a computer. Hence, the motor can be programmable so the particle redirector can take different starting positions so that the particles are distributed into a specific area or into specific areas of the mould during the process. This might be the same area/areas for all the moulds or differ from one mould to another. The AC-servo motor can for example be set so that said particle redirector has, for example 18 free programmable positions, i.e. 18 starting positions. The limitation is that none-usable positions can be avoided. However, the motor and the position control system are not limited to this. It may be free to program the motor so that the particle redirector can be arranged in any position round the pivot axis, i.e. in any angle to a centre axis of the supply duct before it starts pivoting. The programmable position control system can also be set to a specific pivoting direction and pivoting speed so that the particle redirector pivot in a predefined direction and speed in relation to the mat-forming device.

According to another aspect of the present disclosure, there is provided a particle redirector comprising a base, which has convex surface and an opposite concave surface and a peripheral edge. A first imaginary plane is aligned along said pivot axis and bisects said base into two halves such that the cross section of said base at said first imaginary plane is U or V shaped. A second imaginary plane is perpendicular to said first imaginary plane, and said first imaginary plane and said second imaginary plane intersect along said pivot axis. A third imaginary plane bisects said base into two halves, said third imaginary plane is perpendicular to said first imaginary plane and said second imaginary plane, and said third imaginary plane intersects with said first imaginary plane along a first axis and intersects with said second said imaginary plane along a second axis. Said particle redirector comprises at least a first flange and a second flange extending from said convex surface on respective sides of said first imaginary plane and essentially parallel with the first imaginary plane. Said pivot axis is arranged at the centre of gravity of said particle redirector or at distance from said centre of gravity along said first imaginary plane. The same advantages apply as described for the particle redirector in the apparatus above.

In one example embodiment the first imaginary plane bisects said base into two equal halves and said third imaginary plane bisects said base into two equal halves. This way the particle redirector may be symmetric on each side of the first imaginary plane and the third imaginary plane.

In one example embodiment a third flange extends from said convex surface aligned and parallel with said first imaginary plane. The third flange is arranged between the first and the second flange and just as the first and the second flange it helps to direct the particles. The particle director is not limited to have two or three flanges it may more, for example, four or five. The flanges may have a round outer contour or a rectangular shape or any other shape when viewed from the normal direction of said first imaginary plane.

In one example embodiment a fourth flange extends from said convex surface aligned and parallel with said third imaginary plane between said first and said second flange.

In one example embodiment said pivot axis at a cross-section taken along said third imaginary plane is arranged at a substantially equal predetermined distance from a highest point of each said first, second and/or third flange and from an outer point of the peripheral edge on each side of the first imaginary plane.

In one example embodiment said first, second and/or third flange each has a curved outer shape extending from a highest point of each respective flange towards said convex surface, viewed from the normal direction of said first imaginary plane. By having a curved outer shape, it is prevented that fibrous material is piled up on the flanges, which later may fall down and into the mould and create hard areas in the core.

In one example embodiment the particle redirector has an outer contour, formed by the first, second and/or third flanges together with the base, which follows the shape of an imaginary surface of a partially imaginary ellipsoid.

In one example embodiment wherein the first and the second flanges are arranged at a distance from each other.

In one example embodiment the base of the particle redirector has a maximum width at cross section taken along said first imaginary plane.

In one example embodiment said particle redirector comprises a shaft connecting element extending along said pivot axis adapted to house a shaft which is connectable to said shaft connecting element in order to pivot said particle redirector around said pivot axis.

The advantages and clarifications of the above features relating to the particle redirector itself is the same as the advantages and clarifications made to the particle redirector in the apparatus described above.

According to another aspect of the present disclosure, there is provided method of redirecting particles supplied from an opening of a particle supply duct inside a passage which directs said particles towards at least one mould on a movable mat-forming device, which is moving in a machine direction. Said redirection is made with a particle redirector arranged adjacent to said opening. Said particle redirector is pivotable around a pivot axis which is extending in the cross direction to said machine direction of said movable mat-forming device. The method comprises the step pivoting said particle redirector around said pivot axis in the direction along and/or against said machine direction and thereby redirecting said particles to at least one area on said at least one mould. By having the particle redirector pivotable around a pivot axis the particle redirector can redirect the particles from the particle supply duct to a specific predetermined area or areas on the mould. The mat-forming device may be a mat-forming wheel or a mat-forming belt. Both may be provided with a continuous mould extending along the circumference of the device. A continuous mould is utilized when the fibers deposited on the air pervious means are to be used to form a continuous layer, which is subsequently cut into suitable dimensions and shapes to form individual absorbent cores of an absorbent product. Alternatively, a series of separate moulds may be arranged along the circumference of the mat-forming device. Separate moulds are used to directly form cores of a special shape and dimension to form an absorbent core of an absorbent product. The mould on the movable mat-forming device moves along the machine direction and during the movement of the mould the particle redirector may in a first step pivot either in the same direction as the movable mat-forming device or in the opposite direction. Depending on the pivot speed and the pivoting direction the particles can be steered to a specific area or specific areas on the mould. When the mould has been filled with the particles in the specific area the particle redirector can in a second step move in a direction opposite to the first step or in the same direction to a position so that the particle redirector is ready to fill a mould coming after the first mould if the mat-forming device is provided with a series of separate moulds. The particles can be distributed to the same area in all the moulds, or they may differ from one mould to another. Alternatively, several moulds, for example 10 moulds are filled in the same area, and the following ten moulds are filled with particles in a different area. The same applies if it is a continuous mould but then the particles are directed to different positions on the continuous mould so when the individual absorbent cores are cut, they have the particle in their predetermined area.

In one example embodiment said particle redirector is a particle redirector as describe above.

In one example embodiment said particle redirector is from a starting position in a first step pivoting at a first speed in the same direction the mat-forming device or in the opposite direction of the mat-forming device so that particles are directed to a certain area on said mould. The advantage of doing this is that the particles can be distributed in a certain area or areas of the mould, for example at one end of the mould, for example the front of the absorbent core if the front is traveling first in the machine direction. Due to the pivoting the particles can be concentrated in one area more than the other areas of the mould. Hence, the particles are being directed to a certain area, i.e. the particles will follow the intended area on the mould when the mould is moving in the machine direction of the mat-forming device. In traditional particle distribution, for example super absorbent particle distribution, without the pivotable particle redirector the particles would be evenly distributed in the mould. The first speed can be adapted to be such that the particles close to the mould travels with the same speed as the mat-forming device, i.e. the speed of the moulds. If, for example, the particle redirector pivot in the same direction with a first speed which gives particles closest to the mould the same speed and the same direction as the mould the particles will be arranged in the mould in the predetermined area. In order to change the area of the particles in the mould the starting position of the particle redirector itself may be changed. The particle redirector may rotate in a lower speed or a higher speed that the mat-forming device and/or pivot in the same direction or the opposite direction of the mat-forming device. This gives a very flexible system where the particle can be arranged into any area in the mould and the areas can be changed from one mould to another or be the same for several moulds.

In one example embodiment in a second step the particle redirector is pivoting in the opposite direction to the first direction at a second speed which is higher than the first speed. The advantage of doing this is that when the particles have been distributed to a certain area, the particle redirector pivot back to a starting position so that when, for example, a first mould have received particles in its defined area, the particle redirector can be ready to distribute particles to the same area or another area on a following mould. If there is only one mould, which makes one long core which later will be separated into separate cores the same thing happens, specific areas will have more particles than others.

Generally, all terms used throughout this disclosure are to be interpreted according to their ordinary meaning in the technical field, unless explicitly defined otherwise herein. All references to "a/an/the [element, device, component, means, step, etc]" are to be interpreted openly as referring to at least one instance of that element, device, component, means, step, etc., unless explicitly stated otherwise.

Other objectives, features and advantages of the example embodiments of the present disclosure will appear from the following detailed disclosure, as well as from the drawings. The skilled person will readily realize that different features of the example embodiments may be combined to create embodiments other than those expressly described in the following, without departing from the scope of the present disclosure.

BRIEF DESCRIPTION OF THE DRAWINGS

The above, as well as additional objects, features and advantages of the present disclosure, will be better understood through the following illustrative and non-limiting detailed description of example embodiments of the present invention, with reference to the appended drawings, where the same reference numerals will be used for similar elements, wherein:

FIG. 7 shows cross-section B-B in FIG. 5

FIGS. 9a'-9f shows an enlargement of the particle redirector in FIGS. 9a-9f.

FIGS. 9a"-9f" shows a filled mould on the mat-forming wheel in FIGS. 9a-9f in perspective.

Figure 1:
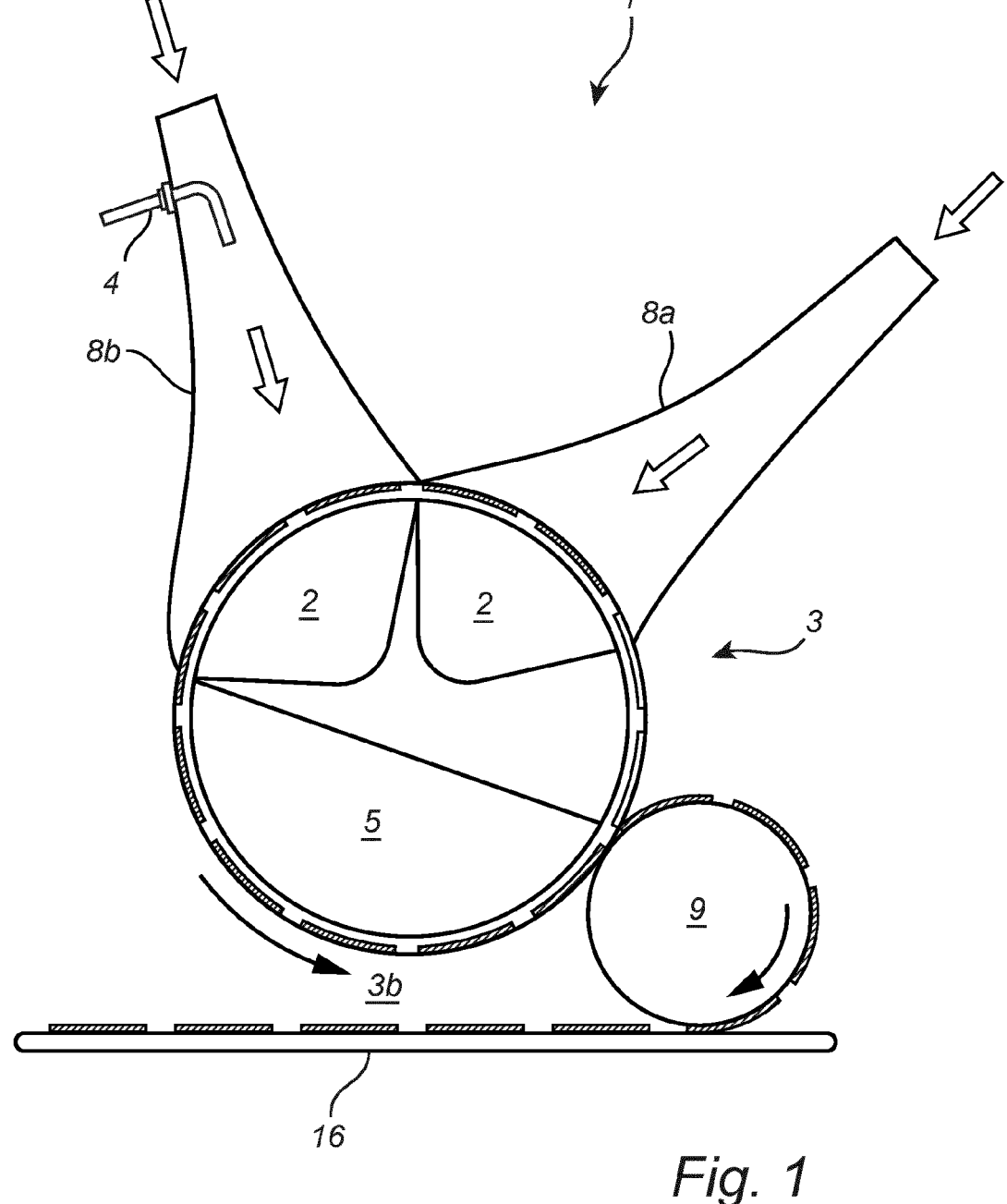
FIG. 1 schematically shows a conventional absorbent core-manufacturing apparatus.

All the figures are highly schematic, not necessarily to scale, and they show only parts which are necessary in order to elucidate the invention, other parts being omitted or merely suggested.

DETAILED DESCRIPTION

Various aspects of the disclosure will now be described more fully hereinafter with reference to the accompanying drawings, in which example embodiments are shown. The example embodiments may, however, take many different forms and should not be construed as limited to the details of embodiment set forth herein; rather, these embodiments are provided for thoroughness and completeness. Like reference characters refer to similar elements throughout the description.

The disclosure refers how to make absorbent cores that can be used in disposable absorbent hygiene products, which means products that are not intended to be laundered or otherwise restored or reused as absorbent products after use, e.g., they are intended, to be discarded after a single use and may also be configured to be recycled, composted or otherwise disposed of in an environmentally compatible manner. By "absorbent product" is meant a product that absorbs or is adapted to absorb bodily fluids, such as urine and/or blood, and/or contain solid excrements.

"Absorbent products" also called disposable absorbent hygiene product or article refer to consumer products which absorb and contain body exudates, and more specifically, refers to products which are placed against or in proximity to the body of the wearer to absorb and contain the various exudates discharged from the body. Absorbent articles, also called absorbent hygiene products, comprise, for example, diapers, sanitary pads, and incontinence pads. Diapers comprise for example all-in-one diapers, pant diapers and belted diapers. The diapers can be diapers for babies, young children or adults.

Figure 2:
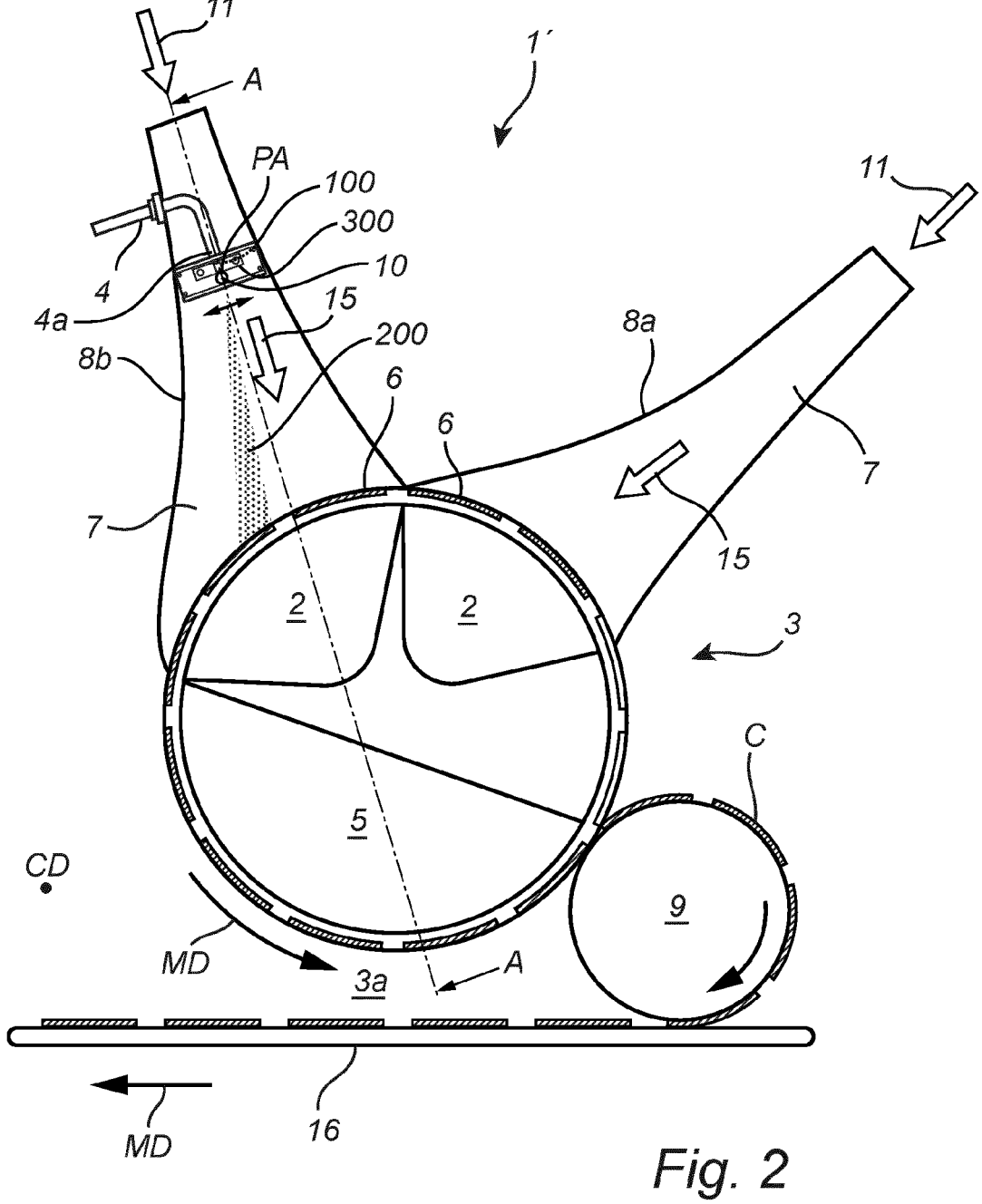
FIG. 2 schematically shows an embodiment of the manufacturing apparatus according to one aspect of the present disclosure with a mat-forming wheel.

In FIG. 2 there is disclosed an apparatus 1' for manufacturing an absorbent core of a liquid-absorbent product according to various aspects of the invention.

The apparatus is a similar apparatus as disclosed in FIG. 1, hence the various parts of the equivalent apparatus have been given the same reference numbers as the parts to which they are generally equivalent.

From a defibration unit (not shown) fibrous material i.e. pulp fibers 11, also called cellulose fluff pulp, are delivered by the aid of an air stream into forming chambers 8a, 8b, here called hoods. The forming chambers i.e. hoods 8a, 8b each forms a passage 7. A mat-forming wheel 3, for formation of a core C of an absorbent product is arranged to rotate under a downstream opening of each hood 8a, 8b and is in sealed connection with said hoods. The mat-forming wheel 3 rotates in the direction shown by arrow 3a, which also is the machine direction MD. In the embodiment according to FIG. 2 the device is provided with two hoods 8a and 8b. Facing each hood opening, non-rotating first suction boxes 2 are arranged inside the mat-forming wheel 3. An air pervious means is arranged along the circumference of the mat-forming wheel 3 to allow air from said suction boxes 2 to pass radially inwards of the mat-forming wheel. An underpressure prevails in the first suction boxes 2 for sucking air from said hoods 8a, 8b through the air pervious means to generate a stream 15 of said radially inwards passing air. Said underpressure may be generated by means of not shown fans.

Fibers 11 delivered to the hoods 8a, 8b are forwarded by the stream 15 towards the circumference of the mat-forming wheel 3 and are deposited there against the air pervious means, which may consist of any net, a plate provided by holes, a fabric or the like (not shown).

The mat-forming wheel 3 may be provided with a continuous mould extending along the circumference of the mat-forming wheel. A continuous mould is utilized when the fibers deposited on the air pervious means are to be used to form a continuous layer, which is subsequently cut into suitable dimensions and shapes to form individual absorbent cores of an absorbent product. In the figure there is shown an example where a series of separate moulds 6 are arranged along the circumference of the mat-forming wheel 3. Separate moulds are used to directly form cores of a special shape and dimension to form an absorbent core of an absorbent product. Variants of moulds are known in the art and need not further be discussed herein.

Often the pulp fibers 11 are combined with other fibers or particles with special properties as added ingredients to form the absorbent cores of absorbent products. Such added ingredients may be super absorbent particles, heat activatable bonding particles or odour absorbent particles. In FIG. 2 super absorbent particles 200 are being added. However, if other particles are to be added they can be added in the same way as the super absorbent particles 200 described in relation to FIGS. 2-11b.

Super absorbent particles are made of absorbent polymer material, so-called super absorbent polymers, of the type that chemically binds large quantities of fluid on absorption with the formation of a fluid-holding gel.

Super absorbent polymers are well-known in the field of absorbent products and are used to help improve the absorbent properties of such products. Super absorbent polymers are constituted by water-swellable and water-insoluble polymers that are capable of absorbing large quantities of fluid upon formation of a hydrogel, such as capable of absorbing at least 5 times their weight of an aqueous 0.9% saline solution as measured according to the method NSWP 241.0.R2 (15). The super absorbent polymers may be inorganic or organic crosslinked hydrophilic polymers, such as polyvinyl alcohols, polyethylene oxides, crosslinked starches, guar gum, xanthan gum, crosslinked polyacrylates, and the like. The polymers may be in the form of powders, granules, microparticles, films, foams and fibers, for example. Upon contact with fluids, such super absorbent polymers swell by absorbing the fluids into their structures. In general, super absorbent polymers can quickly absorb fluids insulted into such articles and can retain such fluids to prevent leakage and help provide a dry feel even after fluid insult.

In the hood 8a pulp fibers 11, only, are used for forming a first layer of the produced core C in the moulds 6.

The second hood 8b is provided with a particle supply duct 4, having an opening 4a, through which the super absorbent particles 200 to be added are injected. In the area of the opening 4a of the particle supply duct 4 a particle redirector 100 is mounted to the hood 8b via connecting plates 300.

Figure 4:
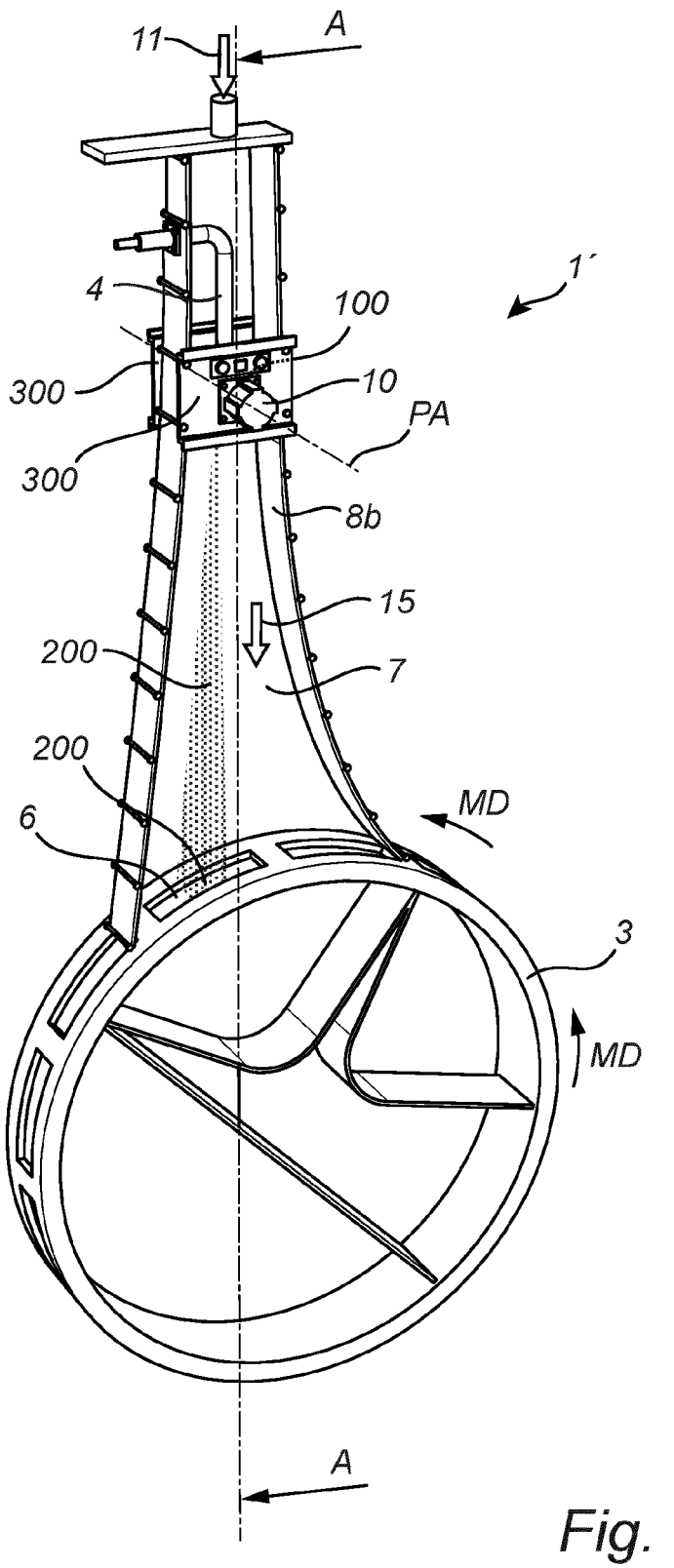
FIG. 4 shows a part of FIG. 2 in perspective.
Figure 5:
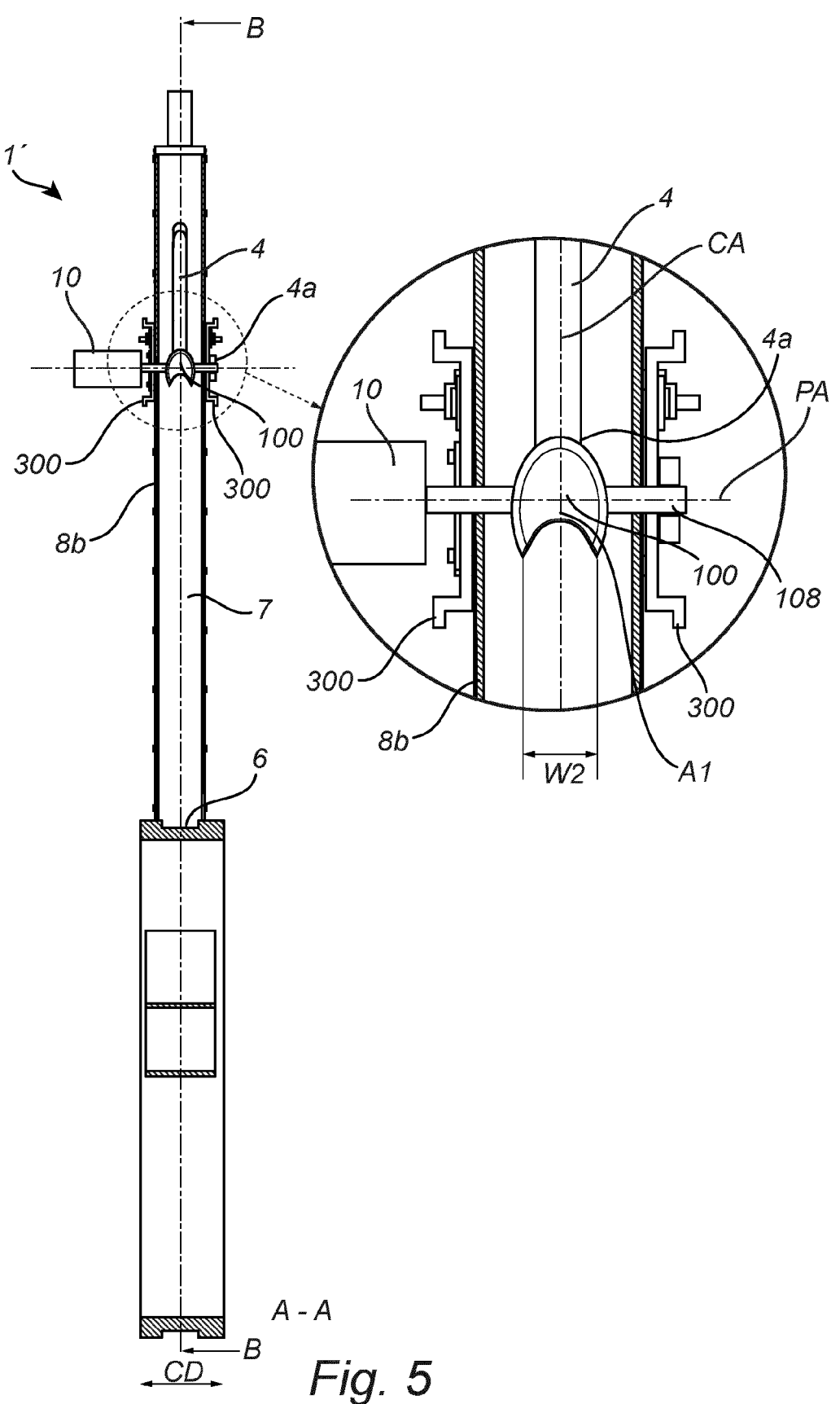
FIG. 5 shows cross-section A-A in FIGS. 2 and 4, but with the particle redirector seen from the side.

See also FIG. 4 and FIG. 5. FIG. 4 shows a part of FIG. 2 in perspective. That is, FIG. 4 shows the second hood 8b and the mat-forming wheel 3 with its moulds 6 in perspective, i.e. with the first hood 8a removed. FIG. 5 shows cross-section A-A in FIG. 2 with the particle redirector seen from the side, i.e. not in a cross-section view.

The super absorbent particles 200 are being redirected by the particle redirector 100 to a predefined area or areas on the mould 6. This will be further described and shown in FIGS. 9a-9f.

The super absorbent particles 200 are being mixed with the pulp fibers 11 in the area underneath the particle redirector 100 and they are being added to the stream 15 to be directed as a mixture of pulp fibers 11 and added particles towards the moulds 6 on the mat-forming wheel 3. Due to the particle redirector 100 the super absorbent particles 200 will be directed to a specific area on the mould 6.

Hence, as the first formed layer rotates from the first hood 8a and enters the second hood 8b, the mixture of pulp fibers 11 and the added super absorbent particles 200 forms a second layer with a higher amount of super absorbent particles 200 in one area on top of the first layer to build up the core of the absorbent product.

According to the prior art technique, as discussed, the completed core in the moulds 6 will be transported on the surface of the wheel 3 to a transfer drum 9 and finally to a conveyor belt 16 (see FIG. 2). The transfer drum 9 may be excluded. To keep the core of fibers adhered to the surface of the mat-forming wheel 3, said wheel is provided with a non-rotating second suction box 5 inside the wheel 3 and exerting a suction effect on the core, such that it will affix to the surface of the wheel. Said second suction box 5 acts along the surface of the mat-forming wheel from the last one of the forming chambers, the hoods 8a, 8b and as far as the core is transported on the wheel 3. In an alternative embodiment the suction box 5 is not acting along the full second arc of the mat-forming wheel, so that it will be easier to let the core leave the mat-forming wheel 3, when said core is delivered to a transfer drum or a conveyor belt 16, without being sucked to the surface.

It shall be realized that in the apparatus only one hood can be provided. For example, if a core should only have one layer of super absorbent particles mixed with pulp fibers. As an end product may consist of several cores, the apparatus for said end product may consists of two or more mat-forming wheels 3, each one of the wheels forming a core, whereupon the two or more resulting cores are assembled to the end product. Each mat-forming wheel may have a similar design as described with for example two hoods, a particle supply duct in one of them and a particle redirector arranged close to the opening of the particle supply duct.

Figure 3:
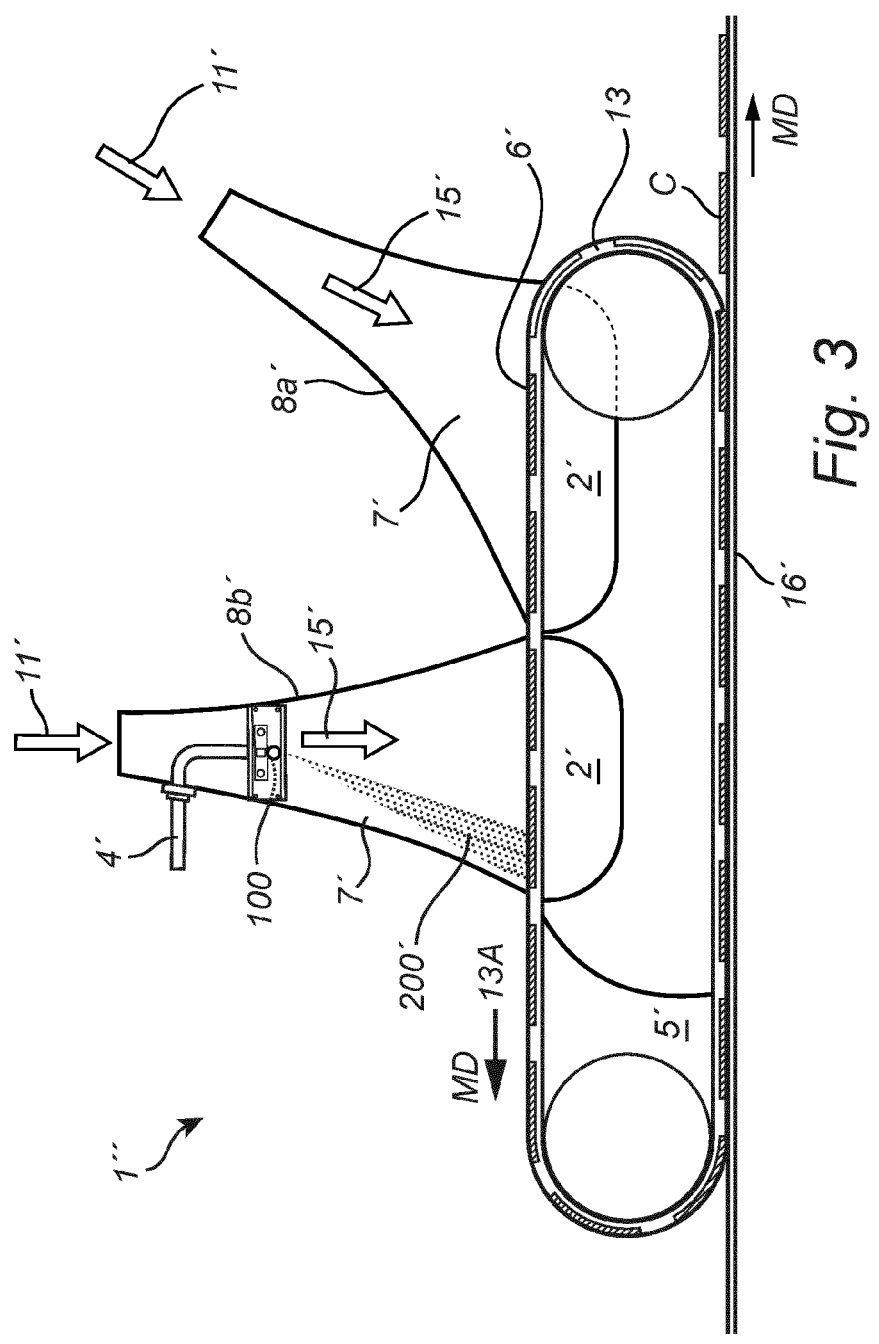
FIG. 3 schematically shows an embodiment of the manufacturing apparatus according to one aspect of the present disclosure with a mat-forming belt.

Alternatively, to a mat-forming wheel a mat-forming belt comprising moulds can be used. FIG. 3 shows schematic an apparatus 1" with a mat-forming belt 13 with moulds 6' on its outer surface. The mat-forming belt 13 may be driven by a driving motor, which could involve a driving of the belt via a gear arrangement (not shown). Just like in FIGS. 1 and 2 the apparatus 1" comprises two hoods 8a' and 8b'. The forming chambers/hoods 8a', 8b' each forms a passage 7'. The mat-forming belt 13, for formation of a core of an absorbent product is arranged to rotate under a downstream opening of the hoods 8a', 8b' and is in sealed connection with said hoods. The mat-forming belt 13 moves in the direction shown by arrow 13*a*, which is the machine direction MD. In the embodiment according to the figure, the device is provided with two hoods 8*a*' and 8*b*'. Facing each hood opening, non-rotating first suction boxes 2' are arranged inside the mat-forming belt 13. An air pervious means is arranged along the circumference of the mat-forming belt 13 to allow air from said suction boxes 2' to pass inwards of the mat-forming belt. An underpressure prevails in the first suction boxes 2' for sucking air from said hoods 8' through the air pervious means to generate a stream 15' of said radially inwards passing air. Said underpressure may be generated by means of not shown fans.

A non-rotating second suction box 5' is arranged inside the belt 13 and exerting a suction effect on the core C, such that it will affix to the surface of the belt until the core C leave the mat-forming belt 13 and is transferred to a transport belt 16'.

Fibers 11' delivered to the hoods 8*a*', 8*b*' are forwarded by the stream 15' towards the mat-forming belt 13 and are deposited there against the air pervious means, which may consist of any net, a plate provided by holes, a fabric or the like.

The mat-forming belt 13 may be provided with a continuous mould extending along the outer surface of the mat-forming belt. In the figure there is shown an example where a series of separate moulds 6' are arranged along the along the outer surface of the mat-forming belt 13 forming separate cores C. A continuous mould is utilized when the fibers deposited on the air pervious means are to be used to form a continuous layer, which is subsequently cut into suitable dimensions and shapes to form individual absorbent cores C of an absorbent product. Separate moulds are used to directly form cores of a special shape and dimension to form an absorbent core of an absorbent product. Variants of moulds are known in the art and need not further be discussed herein.

Just as in FIG. 2, FIG. 3 shows that in the hood 8*a*' pulp fibers 11', only, are used for forming a first layer of the produced core C in the moulds 6'. The second hood 8*b*' is provided with a particle supply duct 4', having an opening through which the particles to be added are injected.

Adjacent the opening of the supply duct 4' is a similar particle redirector 100 as in FIGS. 2-10 arranged. It is attached to the hood via connecting plates. The super absorbent particles 200' are being redirected in the same way as the particles 200 in FIGS. 2-10 and will be further described in FIGS. 9*a*-9*f*. Hence, the function of the particle redirector 100 will be described together with the apparatus 1' in FIG. 2 and FIGS. 4 to 10.

FIG. 5 shows the cross-section A-A in FIG. 2 and FIG. 4, but with the particle redirector 100 seen from the side. The particle redirector 100 is mounted to the hood 8*b* via connecting plates 300. See also FIGS. 4 and 6. The hood 8*b* forms the passage 7 which directs said super absorbent particles towards one mould 6. The particle redirector 100 is pivotable around a pivot axis PA which is extending along the cross-direction CD which is perpendicular to the machine direction MD of the movable mat-forming device 3 so that said particle redirector 100 is pivotable movable along and against said machine direction MD and redirecting said super absorbent particles 200 to different areas on said at least one mould 6. See also FIG. 7, which shows cross-section B-B in FIG. 5. This is done by different surfaces on said particle redirector 100. FIGS. 8*a*-8*d* shows the particle redirector 100 in more detail.

The particle redirector 100 is pivotable around the pivot axis PA by a motor 10 via a shaft 108 (see FIGS. 2, 5 and

Figure 6:
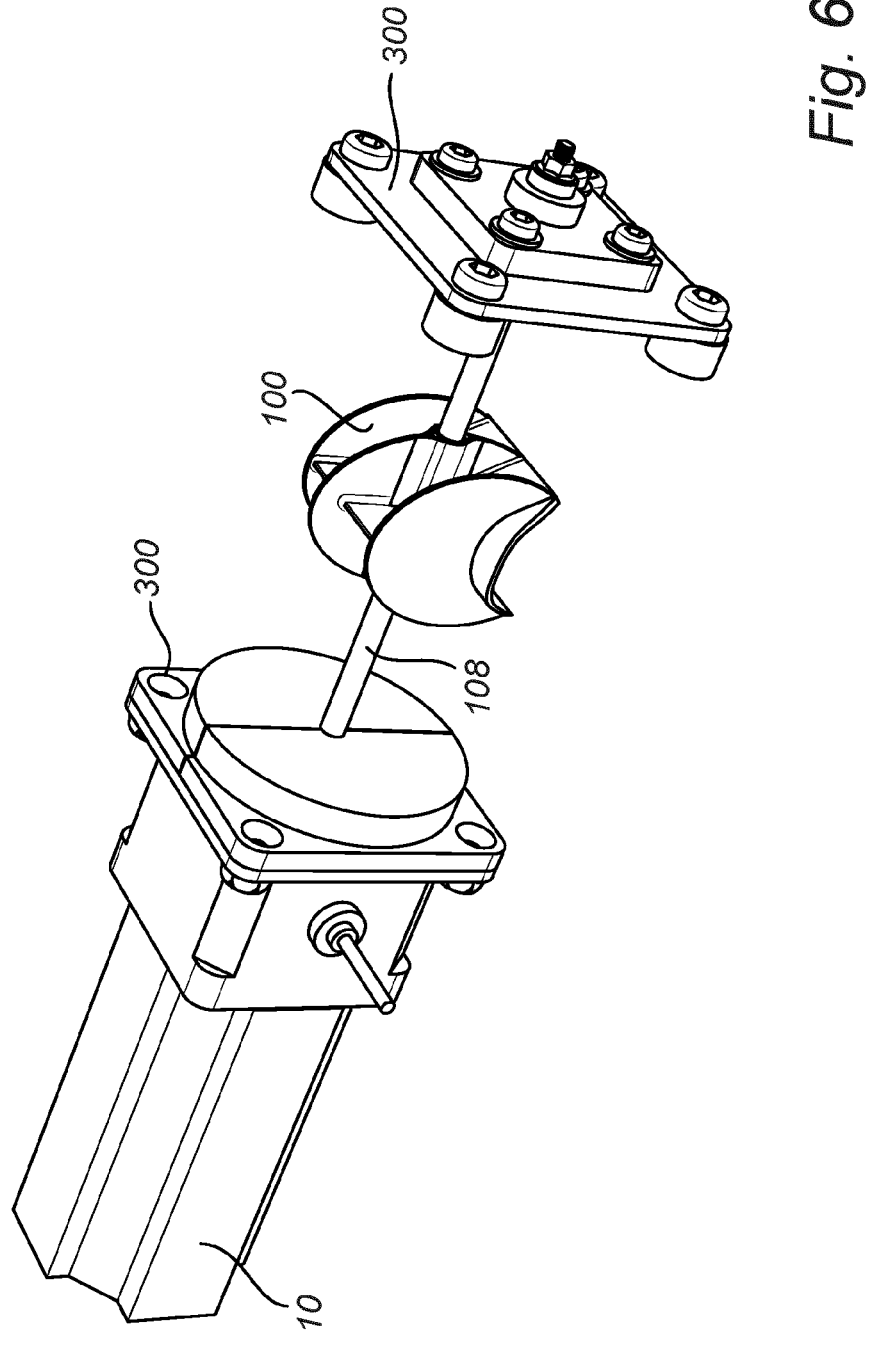
FIG. 6 schematically shows an embodiment of the particle redirector in FIG. 2-5 in perspective connected to a motor and connecting plates.

6) connected to and extending through the particle redirector 100. The motor may be AC-servo motor. FIG. 6 shows the particle redirector 100 in perspective connected to the motor 10 via the shaft 108 and the connecting plates 300 without the hood.

The motor 10 can be steered by a programmable position control system in for example a computer. Hence, the motor can be programmable so the particle redirector can take different starting positions so that the super absorbent particles are distributed into a specific area of the mould 6. This might be the same area for all the moulds 6 or differ from one mould 6 to another. The AC-servo motor can for example be set so that said particle redirector 100 has several distinct redirecting positions, for example 18 free programmable positions, i.e. starting positions. However, the motor and the position control system are not limited to this. It may be free to program the motor so that the particle redirector 100 can be arranged in any position round the pivot axis, i.e. in any angle to a centre axis CA of the supply duct 4.

Figures 8A, 8B:
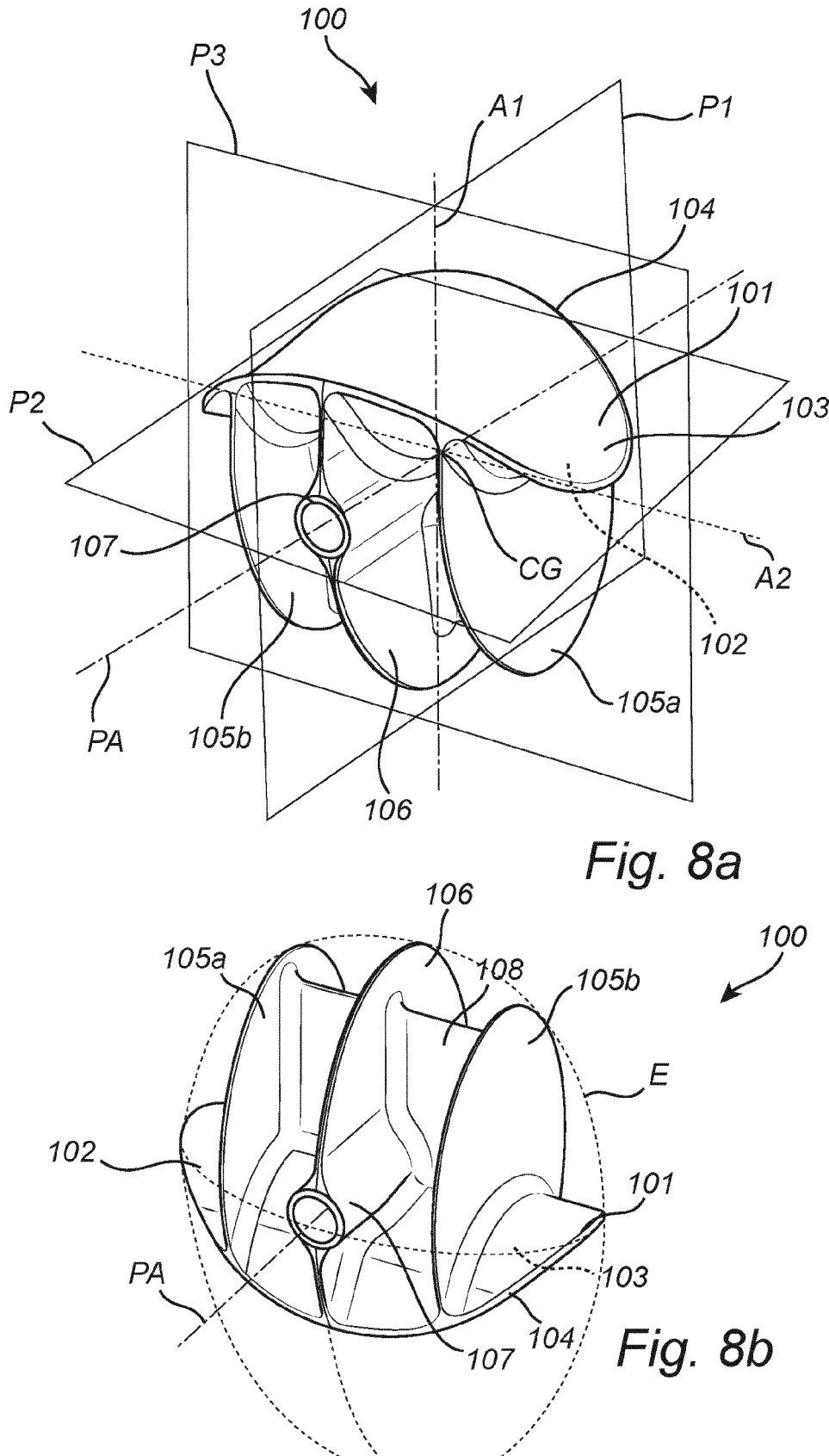
FIG. 8a shows the particle redirector in FIGS. 5, 6, and 7 in perspective with the flanges pointing downwards according to one aspect of the present disclosure.
FIG. 8b shows the particle redirector in FIG. 8a in perspective pivoted 180 degree with the flanges pointing upwardly.

FIGS. 8*a* and 8*b* show the particle redirector 100 in perspective from two different directions. FIG. 8*a* shows the particle redirector 100 in a first direction. FIG. 8*b* shows the particle redirector 100 in a second direction where the particle redirector 100 have been pivoted 180 degree around the pivot axis PA.

The particle redirector 100 comprises a base 101, which has convex surface 102 and an opposite concave surface 103 and a peripheral edge 104. The base 101 has an overall oval shape and a predetermined thickness. The base 101 may alternatively have a round shape or any other shape suitable for the application.

A first imaginary plane P1 is aligned along the pivot axis PA and bisects said base 101 into two equal halves such that the cross section of said base 101 at said first imaginary plane P1 is U- or V-shaped. The base 101 is U-shaped in the figures and can be seen in FIG. 8*d*, which is a view of the particle redirector 100 viewed from the normal direction of the first imaginary plane P1.

A second imaginary plane P2 is arranged perpendicular to said first imaginary plane P1. The first imaginary plane P1 and said second imaginary plane P2 intersect along said pivot axis PA.

A third imaginary plane P3 bisects said base 101 into two equal halves. The third imaginary plane P3 is perpendicular to said first imaginary plane P1 and said second imaginary plane P2. The third imaginary plane P3 intersects with said first imaginary plane P1 along a first axis A1. The third imaginary plane P3 also intersects with said second said imaginary plane P2 along a second axis A2.

The concave surface 103 and the convex surface 102 of the base 101 at a cross section taken along the third imaginary plane P3 is essentially straight and parallel with the second axis. This can be seen in FIG. 8C which show the cross-section taken along the third imaginary plane P3.

The particle redirector 100 further comprising at least two flanges, a first flange 105*a* and a second flange 105*b* extending from said convex surface 102 on both sides of said first imaginary plane P1, and essentially parallel with the first imaginary plane P1. The concave surface 103 or said convex surface 102 together with said flanges 105*a*, 105*b*, direct the super absorbent particles 200 towards the mould 6 when it is mounted in the apparatus 1', 1". The two flanges 105*a*, 105*b* are arranged at the same predetermined distance from the first imaginary plane P1. A third flange 106 extends from said convex surface 102 aligned and parallel with said first imaginary plane P1.

A fourth flange 108 extends from said convex surface 102 aligned and parallel with said third imaginary plane P3. The fourth flange 108 extends between the first flange 105a and the third flange 106 and between the third flange 106 and the second flange 105b. This fourth flange adds mechanical rigidity and if preferably lower than the first, second and third flange 105a, 105b, 106.

The first flange 105a, the second flange 105b and the third flange 106 extending from the convex surface 102 each has a predetermined height. The predetermined height is at highest at a point that is intersecting with the imaginary third plane P3. Each flange also has a predetermined thickness. The thickness can be chosen so that the flanges particle redirector has enough strength. All three flanges 105a, 105b, 106 extend from the peripheral edge 104 on one side the third imaginary plane P3 to the opposite peripheral edge 104. The flanges 105a, 105b, 106 may however extend at a distance from the peripheral edge 104.

Figure 8C:
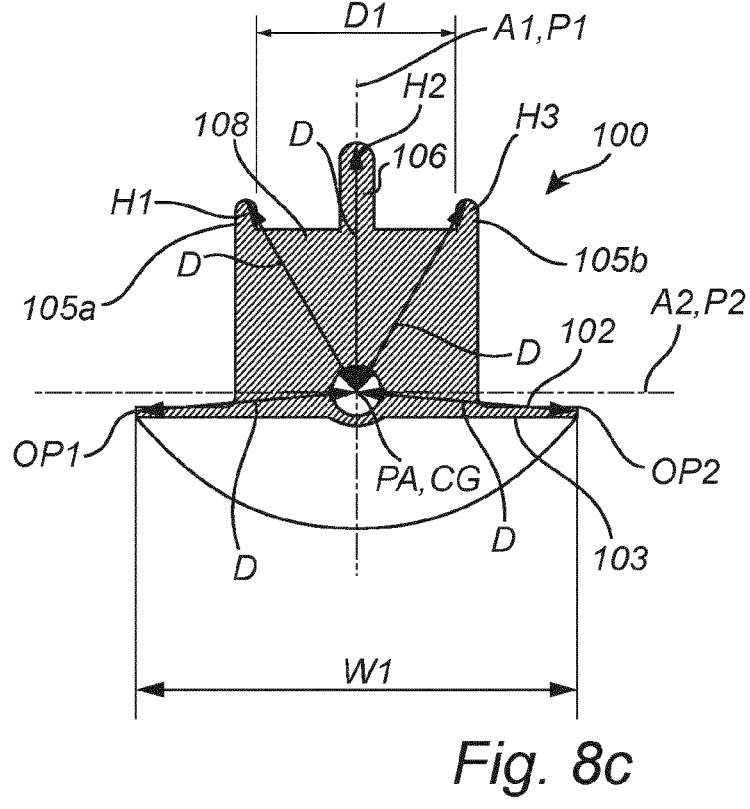
FIG. 8c shows a cross section of particle redirector in FIGS. 8a and 8b taken along the third imaginary plane with the flanges pointing upwardly.

FIG. 8c shows the cross-section of the particle redirector 100 taken along the third imaginary plane P3. The pivot axis PA is arranged at the centre of gravity CG of the particle redirector 100 (See also FIGS. 8a). The pivot axis PA is arranged at a substantially equal predetermined distance D from the highest point H1, H2, H3 of each flange 105a, 105b, 106. The pivot axis PA is also arranged at the substantially same equal predetermined distance D from an outer point OP1, OP2 of the peripheral edge 104 of each side of the imaginary plane P1 in the cross-section taken along the third imaginary plane. Hence, in the cross-section shown in FIG. 8c, i.e. a cross-section taken along the imaginary plane P3 a partial circle can be drawn (not shown) from the first outer point OP1 of the peripheral edge, via the highest points H1, H2, H3 of each flange 105a, 105b, 106 to the second outer point PO2 of the peripheral edge 104 on the opposite side of the first imaginary plane P1, where the centre point of the partial circle coincidence with the centre of gravity CG and the radius of the partial circle is the predetermined distance D.

The first and the second flanges 105a, 105b are arranged at a distance D1 from each other which is essentially equal to the inner diameter DO of the opening 4a of the particle supply duct 4, 4' (see FIG. 7). The distance may however be smaller or larger than the inner diameter of the opening.

The maximum width W1 of the particle redirector 100 at the cross section taken along said third imaginary plane P3, see FIG. 8c and FIG. 7, may be equal or larger than the diameter opening DO of the particle supply duct so that essentially all particles hit the base. In FIG. 7 it is shown that the maximum width W1 is larger than the diameter opening DO of the particle supply duct 4.

Figure 8D:
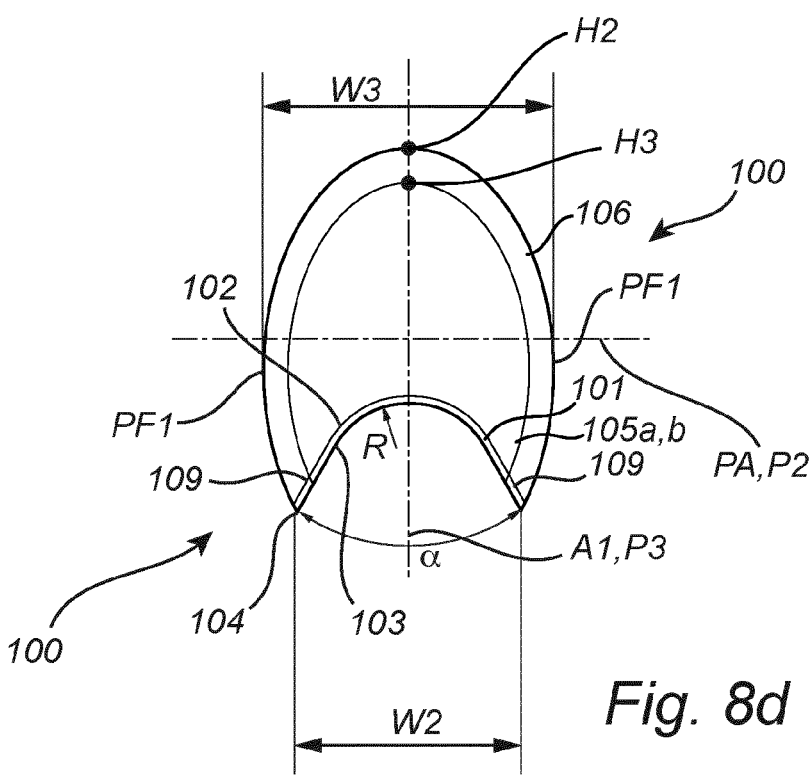
FIG. 8d schematically shows the particle redirector in FIGS. 8a and 8b viewed from the normal direction of the first imaginary plane with the flanges pointing upwardly.

FIG. 8d show the particle redirector 100 when viewed from the normal direction of the first imaginary plane P1. The maximum width W2 of the base 101 of particle redirector 100 is larger than the diameter opening of the particle supply duct 4 so that essentially all particles hit the particle redirector.

The maximum width W3 of the particle redirector 100 is larger than the maximum width W2 of the base 101. The maximum width of the base and the particle redirector is at a cross section taken along the first imaginary plane P1.

The flanges 105a, 105b, 106 each has a curved outer shape which can be seen in FIG. 8d and it is curved from its highest point H1, H2, H3 downward to the peripheral edges 104 on both sides of the third imaginary plane P3, i.e. on both sides of the axis A1. That is the first, second and/or third flange each has a curved outer shape starting from said highest point towards said convex base 102, viewed from the normal direction of said first imaginary plane P1

The outer contour of the third flange 106 is symmetrical on both sides of the axis A1 from its highest point H2 to a point PF1 at the maximum width W3 of the particle director and from that point PF1 curved towards the outer edge 104 of the base. The first and the second flange 105a, 105b has a matching curvature. The curvature is such that the base 101 and the first, second and third flanges 105a, 105b, 106 extending from the convex surface 102 the particle redirector 100 on the convex side 102 of the base 101 gets an overall shape of a part of an imaginary ellipsoid E, see FIG. 8b. That is, the outer contour of the first, second and thirds flanges 105a, 105b, 106b together with the base 101 follows the shape of an imaginary surface of a partially imaginary ellipsoid E.

Figure 10:
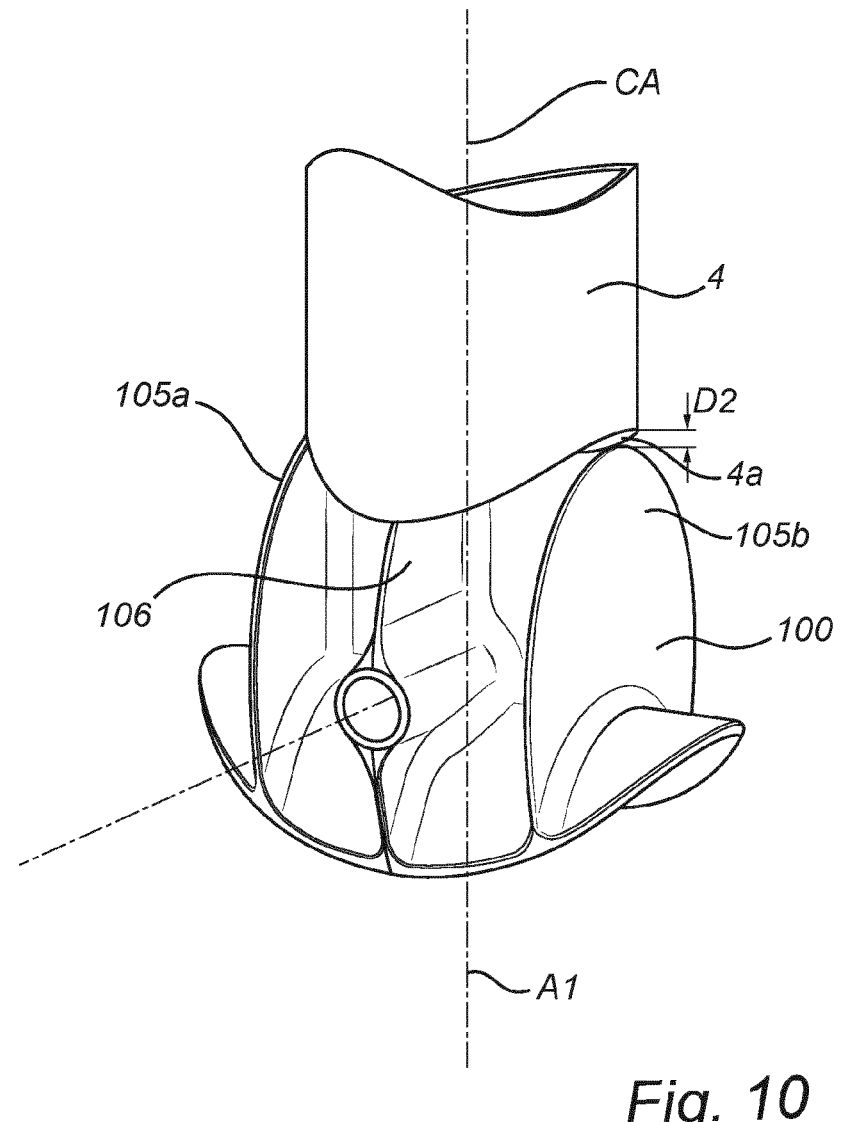
FIG. 10 show the particle redirector and the particle supply duct in FIGS. 5 and 7 in an enlarged view and in perspective.

As shown in FIGS. 5 and 7 the particle redirector 100 is arranged close to the opening 4a of the particle supply duct 4. FIG. 10 shows the particle redirector 100 and the particle supply duct 4 in FIGS. 5 and 7 in in perspective and enlarged. The first axis A1 of said super absorbent particle redirector 100 is aligned with the centre axis CA of said particle supply duct 4.

The second flanges 105a, 105b are aligned with the wall of the particle supply duct 4 and the third flange 106 extends into the opening 4a of the particle supply duct 4. The end of the particle supply duct 4, i.e. at the opening 4a, is adapted to the particle redirector 100. The end may be so designed that when parts of the flanges of the particle redirector 100 protrude into the opening of the particle supply duct 4 the particle redirector 100 can pivot, i.e. rotate without hitting the particle supply duct 4. For example, the end of the particle supply duct 4 may have a matching form to the outer contour of the first, second and thirds flanges 105a, 105b, 106b which together with the base 101 follows the shape of an imaginary surface of a partially imaginary ellipsoid. That is, the end of the particle supply duct 4 may have a shape that corresponds to the imaginary surface of the partially imaginary ellipsoid. As can be seen in FIG. 5 and especially in FIG. 10 the end of the particle supply duct 4 has a concave shape when viewed from the normal direction of said first imaginary plane P1 of said particle director and a convex shape when viewed from the normal direction of said third imaginary plane P3 of said particle director (see FIG. 8a for the planes). Hence, the end of the particle supply duct 4, which forms the opening has as concave/convex extension around the circumference of the particle supply duct 4. Preferably, the particle director 100 is arranged such that is a minimal space, i.e. a distance D2, between the first flange 105a and the end of the particle supply duct 4 when the flanges is parallel with the centre axis CA of the particle supply duct 4 and pointing towards the opening 4a. The same applies for the second flange 105b and the third flange 106. Due to the distance D2 being the same for the first, second and third flanges 105a, 105b, 106 and the end points PO1 and PO2 from the pivot axis PA and the shape of the flanges which follows the shape of an imaginary surface of a partially imaginary ellipsoid the particle director 100 will not hit the particle supply duct 4 while pivoting. The space between the flanges and the end of the particle supply duct 4 is preferable minimized in order to reduce uncontrolled airflows into unwanted directions. The distance may be 1-4 mm, more preferably 2 mm. An example of a particle redirection in FIGS. 8a-8d will now be described. If for example the inner diameter DO of the particle supply duct 4 is 46 mm with a 2 mm wall, the particle director 100 made of stainless steel may have the following dimensions:

The oval base is 2 mm thick and curved with a radius R (see FIG. 8d) on the concave side, forming a curved portion. The radius is 18 mm. On each side of the axis A1 the base transitions from the curved portion to a flat portion 109. The angle α between the flat portions 109 is 60 degree. The base is not limited to have flat portions, it may also be one curved portion.

The maximum width W2 of the base is 49 mm. W3 is 60 mm. The predetermined distance D between the pivot axis PA and the highest point H1, H2, H3 of each flange 105a, 105b, 106 and between the pivot axis PA and each outer point OP1, OP2 of the peripheral edge 104 is 45 mm. Hence if a curve is drawn between the outer points OP1, OP2 and the highest points H1, H2, H3 of each flange 105a, 105b, 106 a partial circle can be drawn. The partial circle will then have a radius which is 45 mm. The centre axis of the circle being aligned with the pivot axis PA The maximum width W1 of the base 101 at the cross section taken along the plane P3 is approximately 90 mm.

The flanges 105a, 105b, 106 each have a thickness of 1 mm. The outer contour of the third flange 106 when viewed from the normal direction of said first imaginary plane P1 is symmetrical curved on both sides of the axis A1 from its highest point H2 to a point PF1 at the maximum width W3 of the particle director and from that point PF1 curved towards the outer edge of the base.

The outer contour of the first and the second flange 105a, 105b follows the outer contour of the third flange 106 with a distance. The distance shall be chosen so the particle director gets an overall shape of a partially imaginary ellipsoid E.

In this example, the opening of the particle supply duct 4 is arranged at a distance from the movable mat-forming device. The distance is here 150 cm, such that the fibrous material and the particles can mix before they reach the mould. The particle redirector 100 protrude into the particle supply duct 4 and particles will be mixed the fibrous material before they reach the mould.

FIGS. 5, 7 and 10 show that parts of the particle redirector extend into the particle supply duct 4, however the particle redirector 100 is not limited to this, it can be arranged at a distance from the opening. The distance should be chosen so that approximately all particles from particle supply duct 4 hits the particle redirector 100.

The particle redirector 200 further comprises a shaft connecting element 107 (see FIGS. 8a and 8b) extending along said pivot axis PA adapted to house a shaft 108 which is connectable to said shaft connecting element 107 in order to pivot said particle redirector around said pivot axis PA see FIGS. 5 and 6. The shaft connecting element 100 is here illustrated as having a cylindrical shape within the particle redirector 100 with an opening through which the shaft extends and is connected with.

The particle redirector 200 is made of stainless steel. However, any other material which is strong and wear resistant can be used.

The flanges 105a, 105b, 106 of the particle redirector 100 and the form of the oval base 101 has been described that they together form an overall shape of a part of an imaginary ellipsoid E, see FIG. 8b. That is, the outer contour of the first, second and thirds flanges 105a, 105b, 106b together with the base 101 follows the shape of an imaginary surface of a partially imaginary ellipsoid E. However, the particle redirector is not limited to this. The first, the second and the thirds flanges 105a, 105b, 106b may have another curved shape when viewed from the normal direction of the first imaginary plane P1.

They may even be rectangular shaped. The end of the particle supply duct 4 will hence then be adapted to the shape of the particle redirector.

FIGS. 9a-9f shows the apparatus 1' in FIG. 4 with the pivotable particle redirector 100 described and shown in FIGS. 8a-8d in different starting positions inside the hood 8b. Based on the starting position of the particle redirector 100 in relation to the outlet 4a of particle supply duct 4, the pivot direction and the pivot speed of the particle redirector 100 the super absorbent particles 200 can be distributed to at least one area on the mould 6. That is, the particle redirector 100 comprises redirecting surfaces, which are adapted to redirect said super absorbent particles 200 in the machine direction MD and/or in the cross direction CD to said machine direction MD, depending on the position of the particle redirector 100 inside said passage 7. The redirecting surfaces of said particle redirector 100 are the convex surface 102 together with the first, second, third and fourth flanges 105a, 105b, 106, 108 or the concave surface 103.

The apparatus 1' in FIGS. 9a-9f, which is the same apparatus as shown in FIGS. 4-7, redirects the super absorbent particles 200 towards one mould 6 on the movable mat-forming device 3 which is moving in the machine direction MD. In the mould 6 an absorbent core will be formed. An absorbent core comprises a front portion, a back portion and a crotch portion positioned between the front portion and the back portion. The core has a longitudinal axis extending along a length of said core and crossing said front, crotch and back portions, the absorbent core having a width extending perpendicular to said length and a perimeter comprising at least two opposing ends and at least two opposing sides positioned between said ends. The shape of the mould 6 forms the outer contour of the core and the longitudinal axis AC of the mould extends in the machine direction MD so the leading portion 6a of the mould 6 may be the part that form the front portion of the absorbent core and the trailing portion 6b may form the rear portion of the absorbent core and the middle portion 6c between the leading portion 6a and the trailing portion 6b forms the crotch portion (See FIGS. 9a"-9f"). In the following examples the leading portion 6a of the mould will form the front portion of the core and the trailing portion 6b will form the rear portion of the core, but it may however be the other way around.

In FIGS. 9a-9f the particle redirector 100 is for illustrational reasons arranged at a minor distance from the opening 4a of the particle supply duct 4 compared to the particle redirector 100 in FIGS. 4-7, but it will work in the same way if arranged according to what is described in FIGS. 4-7 as long a major part of the super absorbent particles hits the particle redirector.

Figure 9A:
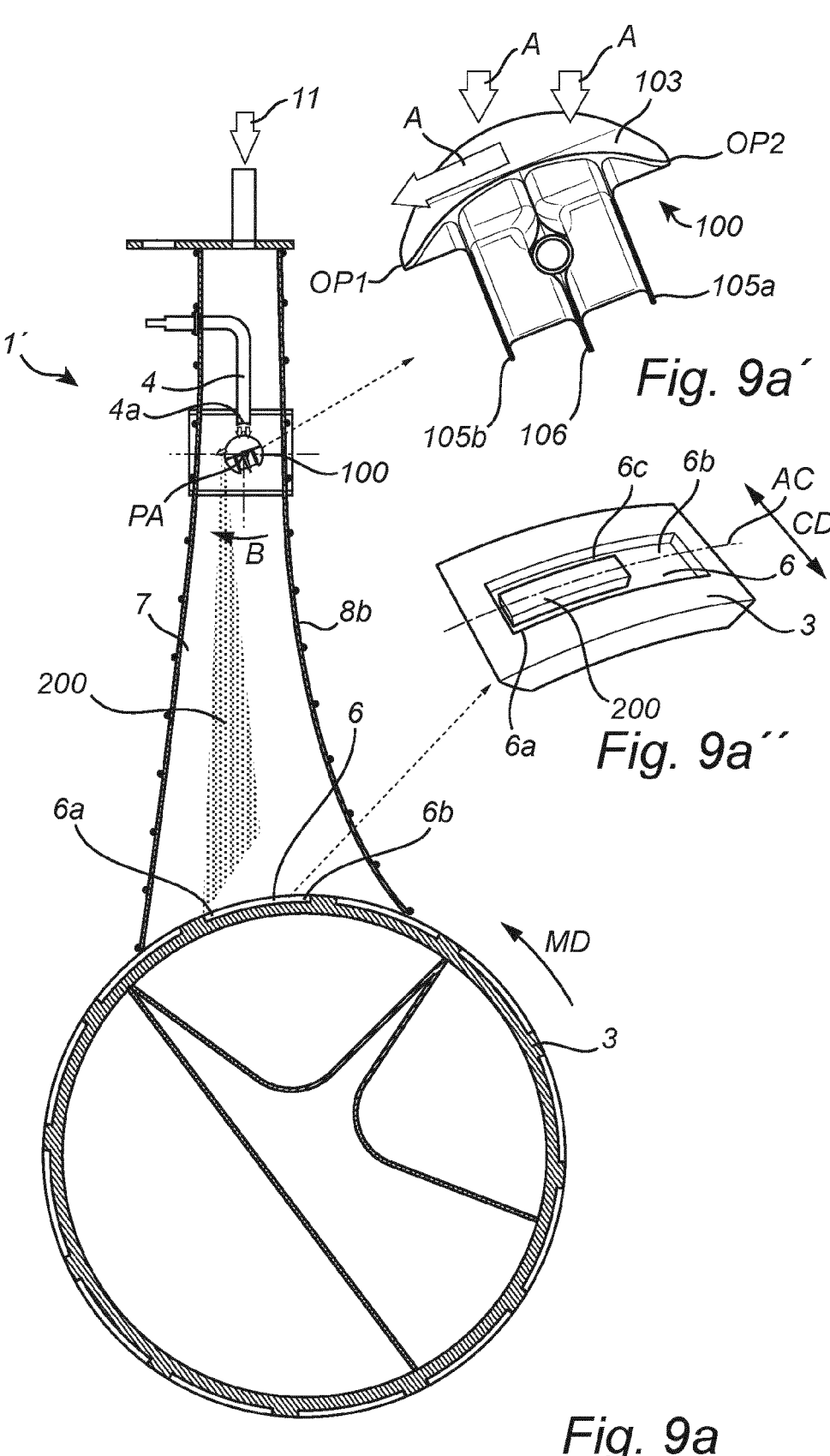
FIGS. 9a-9f schematically show the particle redirector in FIG. 8a-8d in different positions in the manufacturing apparatus in FIG. 7, i.e. cross-section B-B in FIG. 5, but with the particle redirector from the side.

The redirection of the super absorbent particles 200 is made with the particle redirector 100 which is arranged adjacent to said opening 4a and said particle redirector 100 is pivotable around the pivot axis PA which is extending in the cross direction CD to said machine direction MD of said movable mat-forming device 3. FIGS. 9a'-9f' are each an enlargement of the particle redirector 100 in their respective FIGS. 9a-9f, but shown slightly in perspective, for illustration purpose, where the arrows A symbolise the direction the super absorbent particles 200 will hit the particle redirector 100 and the direction they continue after hitting the particle redirector 100.

In order to distribute the super absorbent particles 200 to specific areas the particle redirector 100 needs to pivot during the process. If the particle redirector 100 is stationary the super absorbent articles 200 would be equally distributed over the entire length of the absorbent core. Hence the apparatus 1' is during manufacturing pivoting the particle redirector 100 around the pivot axis PA in the direction along and/or against said machine direction MD and thereby directing said super absorbent particles 200 to different areas on said at least one mould 6.

In FIG. 9a the particle redirector 100 is positioned in a starting position where the concave surface 103 is facing the opening 4a of the particle supply duct in a slightly angled position so that the super absorbent particles 200 are directed by the concave surface 103 more towards the leading portion 106a of the mould 6 when entering the hood 8b. So when the super absorbent particles are coming from the particle supply duct 4 (Arrows A in FIG. 9a') they hit the concave surface 103 and slides downwards the concave surface towards the outer edge OP1 before falling downwards towards the mould 6. In a first step, at the same time as the super absorbent particles are entering the passage 7 and hits the particle redirector 100, the particle redirector 100 is pivoting in a first direction, arrow B, in a first speed. The first speed should be such that the super absorbent particles close to the mould 6 is traveling with the same speed and in the same direction as the mat-forming device 3, i.e. in the machine direction MD so that super absorbent particles 200 are directed to the leading portion 6a of the mould 6 and along the centre line AC of the mould which is extending in the machine direction MD. The result of this can be seen in FIG. 9a''. Due to the pivoting of the particle redirector the super absorbent particles 200 will be concentrated in one area more than the other areas of the mould 6. Hence, the absorbent core will in this case have more super absorbent particles 200 in the front portion 6a and along its centre line AC. However, it should be realized that also some particles may come in the other areas.

As the opening 4a of the particle supply duct 4 is arranged at a distance from the movable mat-forming wheel 3 such that the fibrous material 11 and the super absorbent particles 200 can mix before they reach the mould. The area provided with super absorbent particle 200 in the mould 6 shown in FIG. 9a'' particles will be mixed the fibrous material 11. The area around the super absorbent particle 200 in the mould will also be provided with fibrous material (not shown) since the fibrous material 11 is applied continuously throughout the process.

In a second step the particle redirector 100 is pivoting in the opposite direction to the first direction back to the starting position at a second higher speed. The advantage of doing this is that when the super absorbent particles have been distributed to a specific area, the particle redirector 100 pivots back to its starting position so that when, for example, a first mould 6 have received super absorbent particles in its predefined area, the particle redirector can be ready to distribute the super absorbent particles to the same predetermined area on a following mould 6. If there is only one mould, which makes one long core which later will be separated into separate cores the same thing happens, specific areas will have more super absorbent particles than others. Alternatively, instead of pivoting back i.e. in the opposite direction to the first direction, the particle redirector can continue pivot in the same first direction at a second higher speed back to its starting position.

The apparatus in FIGS. 9b-9f works in the same way, however the starting position of the particle redirector 100 is different in order to distribute the super absorbent particles in different areas in the mould. Only the starting positions are described for FIGS. 9b-9f and how the super absorbent particles 200 will be distributed in the mould 6 as a result of the starting position. The pivoting of the particle redirector 200, i.e. the speed and direction in both the first and the second step is the same as described for FIG. 9a. The rotation of the mat-forming wheel, i.e. direction and speed, is in the same way as described for FIG. 9a. It shall however be understood that the pivoting direction can also be against the machine direction depending on how the particle redirector is positioned in its starting position and where the particles are wanted in the mould. For example, for FIG. 9a if the pivoting direction in the first step was against the machine direction more particles would be along the centre line AC. It shall be realized that the particle redirector 100 can be programmed to move with different speeds and in different direction so that the particles can be distributed as desired within the mould. It shall also be realized that the starting position from one mould to another may differ so that the core formed in one mould differ from one core formed in another mould, for example the mould next to the first mould.

Figure 9B:
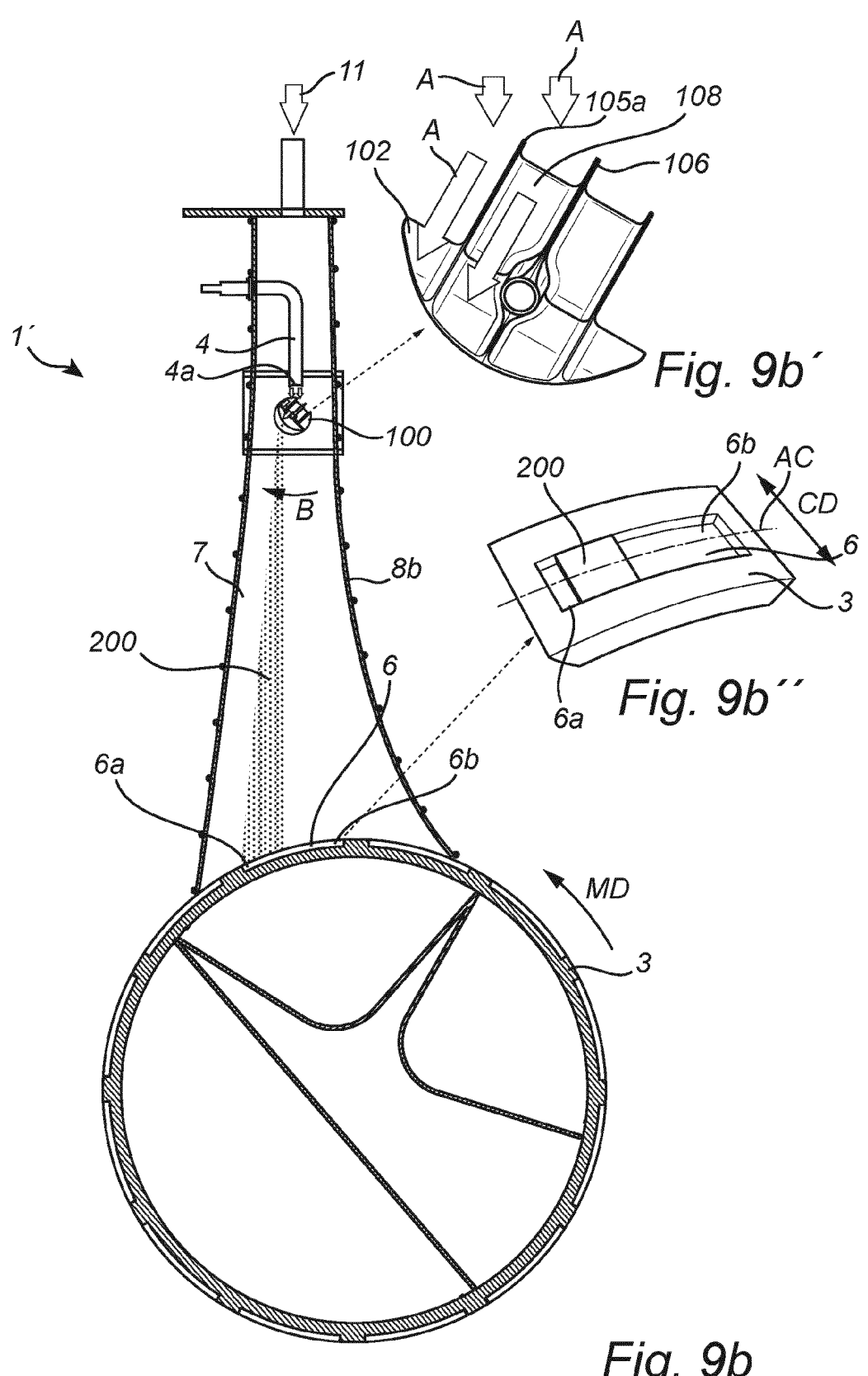

In FIG. 9b the particle redirector 100 is positioned so that more super absorbent particles 200 are distributed more towards the leading portion 6a of the mould 6 entering the hood 8b but also more in the cross-direction CD of machine so that the whole width of the mould 6 in that area may get super absorbent particles, see FIG. 9b''. This gives more super absorbent particles 200 in the front of the core but also over the whole width of the core. This is accomplished by having the particle redirector, in its starting position, in an angle to the opening 4a with the flanges 105a, 105b, 106 facing the opening 4a of the particle supply duct in a slightly angled position so that the super absorbent particles 200 are directed, see arrows A in FIG. 9b', by the flanges and the convex surface 102. The super absorbent particles 200 are especially directed by the first flange 105a and the third flange 106 and also the fourth flange 108 towards the leading portion 6a and over the whole width of the core at that position since the particles also slides one the convex surface 102 on both sides of the fourth flange 108.

Figure 9C:
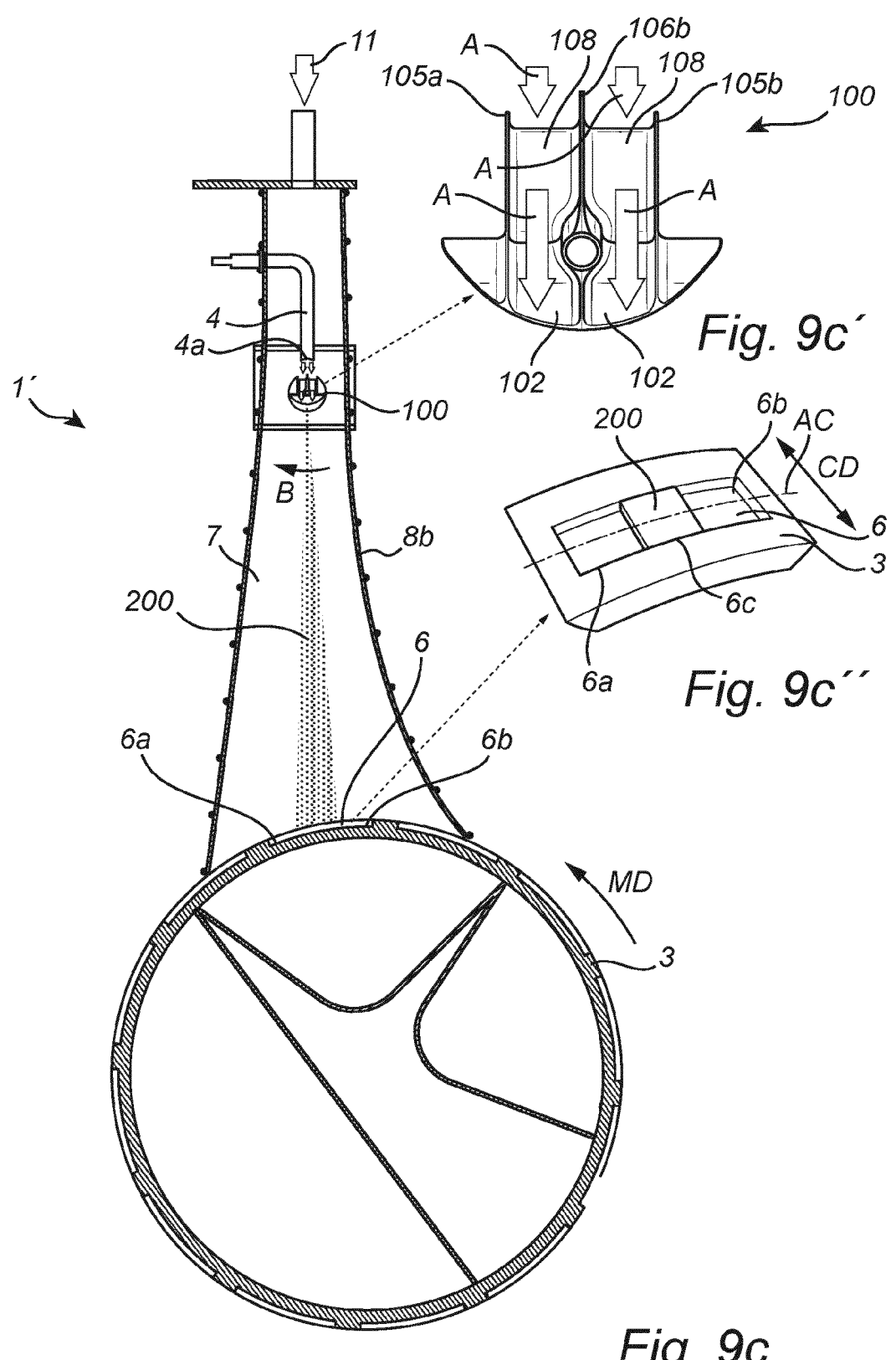

In FIG. 9c the particle redirector 100 is positioned so that more super absorbent particles 200 are distributed more towards the middle portion 6c between the leading portion 6a and the trailing portion 6b of the mould 6 but also more in the cross-direction CD of machine so that the whole width of the mould 6 in that area may get super absorbent particles 200, see FIG. 9c''. This gives more super absorbent particles 200 in the crotch portion of the core but also over the whole width of the core. This is accomplished by having the flanges of particle redirector 100, in its starting position, pointing towards the opening 4a of the particle supply duct so that the super absorbent particles 200 are directed, see arrow A in FIG. 9c' by the flanges 105a, 105b and the convex surface 102 and also the fourth flange 108 towards the middle portion 6c. The super absorbent particles will hit the particle director 100 on both sides of the fourth wall 108, hence the particles 200 will be directed over the whole width of the mould 6.

Figure 9D:
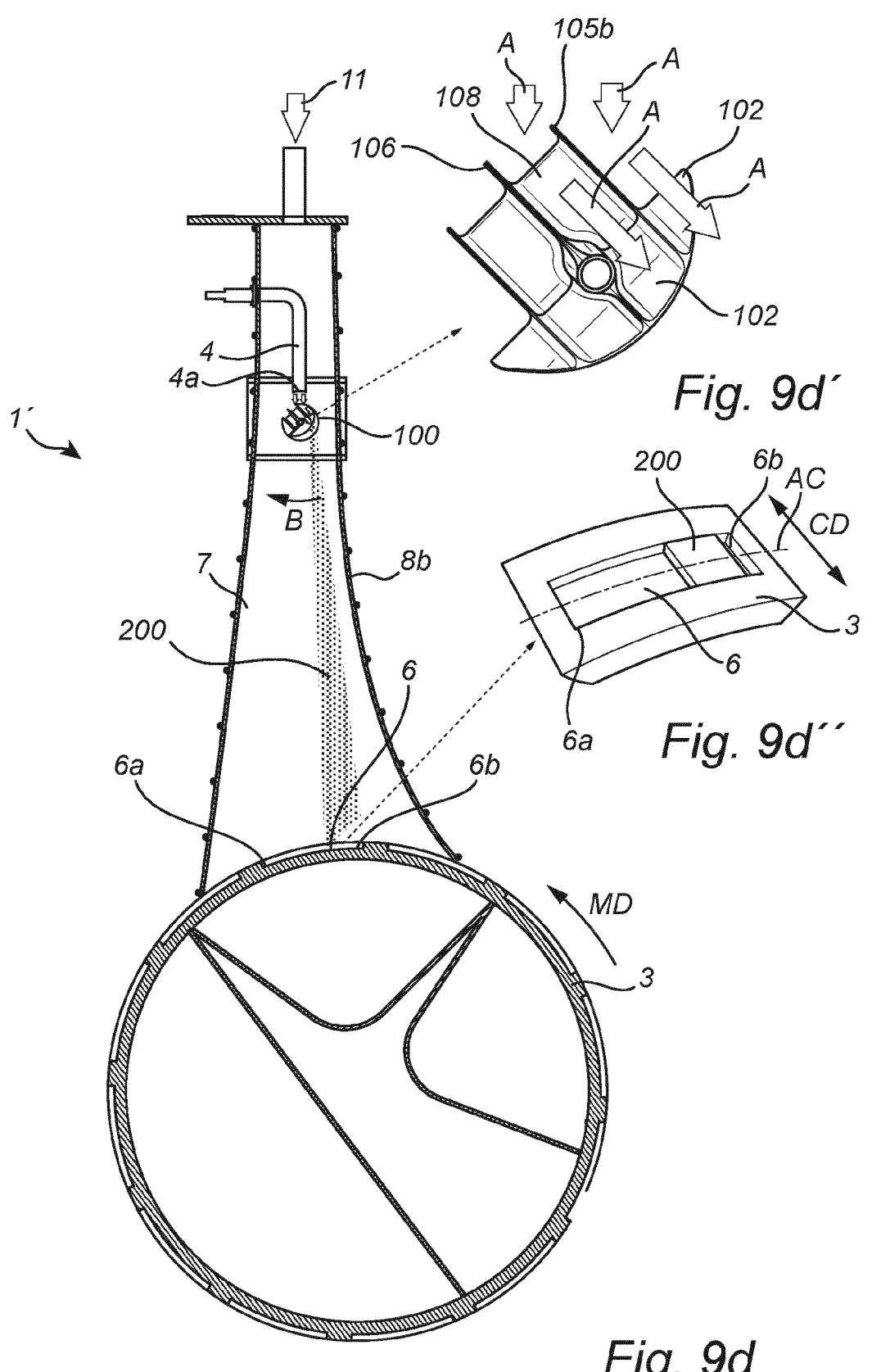

In FIG. 9d the particle redirector 100 is positioned so that more super absorbent particles 200 are distributed more towards the trailing portion 6b of the mould 6 but also more in the cross-direction CD of machine so that the whole width of the mould 6 in that area may get super absorbent particles, see also FIG. 9d''. This gives more super absorbent particles 200 in the rear portion of the core but also over the whole width of the core. This is accomplished by having the particle redirector 100, in its starting position, in an angle to the opening 4a of the particle supply duct 4 with the flanges facing the opening 4a of the particle supply duct in a slightly angled position, however in an opposite direction of FIG. 9*b* so that the super absorbent particles 200 are directed, see arrow A in FIG. 9*d*' by the flanges and the convex surface 102, and especially of the second flange 105*b* and the third flange 106 and also the fourth flange 108 towards the trailing portion 6*b*. The super absorbent particles 200 will also hit the convex surface 102 of particle director 100 on both sides of the fourth wall 108, hence the particles 200 will be directed over the whole width of the mould 6.

Figure 9E:
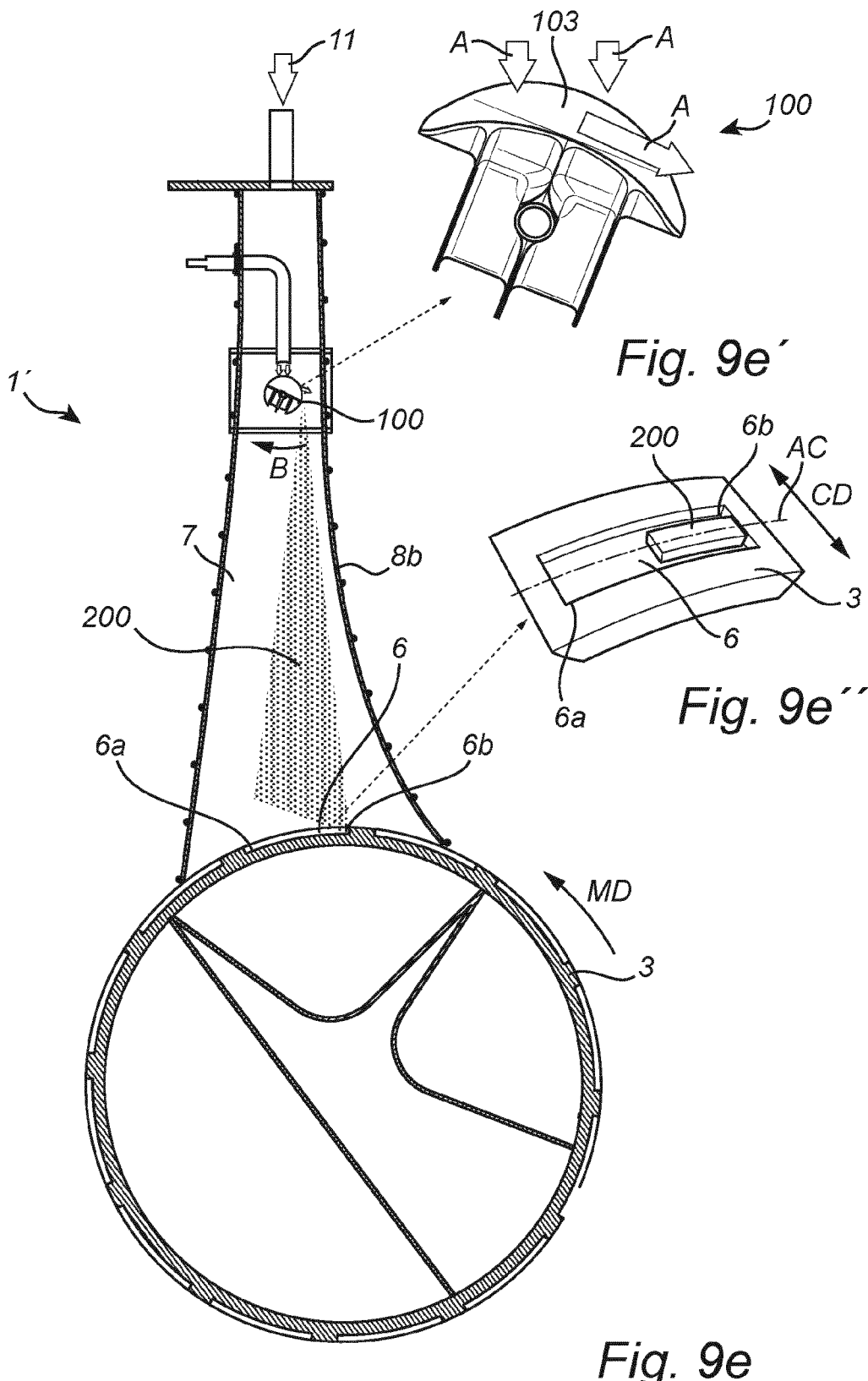

In FIG. 9*e* the particle redirector 100 is positioned so that more super absorbent particles 200 are distributed more towards the trailing portion 6*b* of the mould 6 along the centre line AC, see FIG. 9*e*''. This is accomplished by having the concave surface 103 facing the opening 4*a* of the particle supply duct in a slightly angled position however in an opposite direction of FIG. 9*a*. By having this starting position, the super absorbent particles 200 are directed, see arrows A in FIG. 9*e*', by the concave surface 103 more towards the trailing portion 6*b* of the mould 6.

Figure 9F:
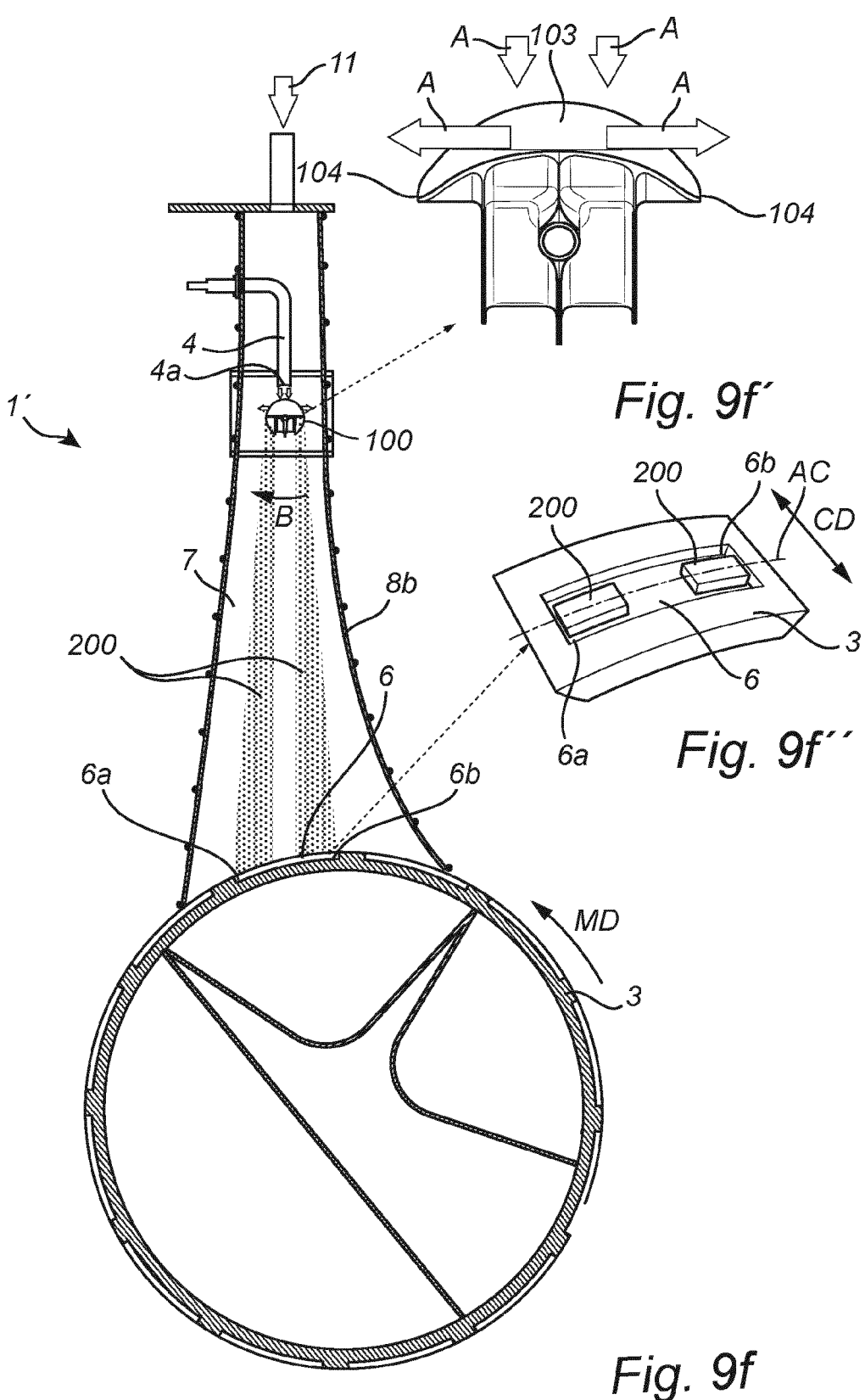

In FIG. 9*f* the particle redirector 100 is positioned so that more super absorbent particles 200 are distributed both towards the leading portion 6*a* and the trailing portion 6*b* and along the centre line AC of the mould 6, see also FIG. 9*f*''. This gives more super absorbent particles 200 in both the front portion and the rear portion of the core along the centre line AC. This is accomplished by having the concave surface 103 of the particle redirector 100 facing the opening 4*a* of the particle supply duct 4 in the starting position, so that the super absorbent particles 200 are directed, see arrows A in FIG. 9*f*, by the concave surface 103 in two directions so the super absorbent particles when they hit the concave surface 103 may get directed in either direction and fall over the outer peripheral edge 104 towards the mould 6.

The different starting positions of the particle redirector 100 is not limited to the ones described in FIG. 9*a*-9*f*. They may be any position there between. The positions can be set and adjusted by a computer program which steers the motor. The position of the super absorbent particles within the mould can be manipulated by the starting position of the particle redirector relative the mould, the position of the base and/or the flanges of particle redirector relative the opening of the particle supply duct, the speed of the pivoting of the particle redirector and/or the pivoting direction.

The particles described in relation to the figures are described being super absorbent particles. However, it should be realized that other particles such as heat activatable bonding particles or odour absorbent particles may also be distributed in similar way.

Figures 11A, 11B:
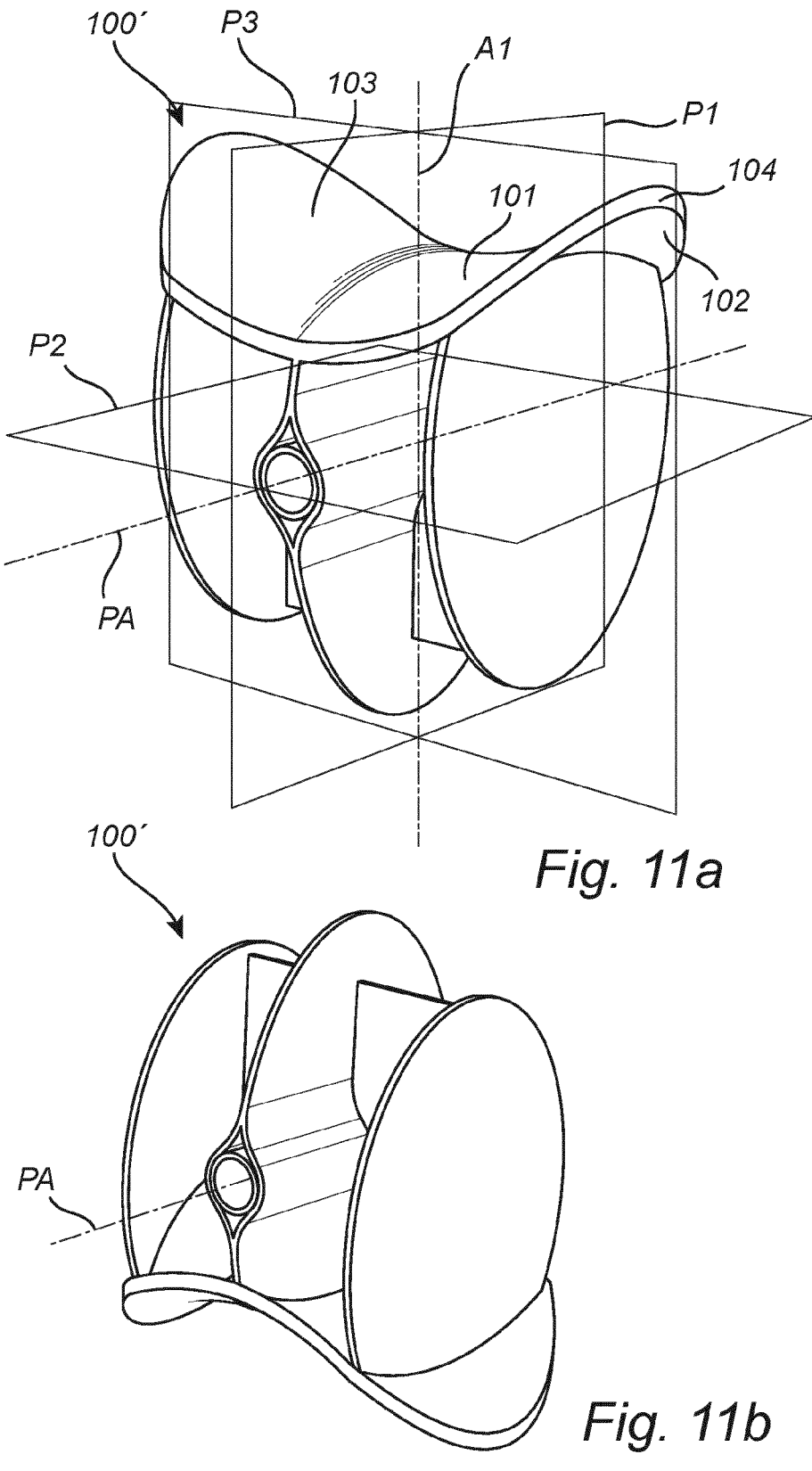
FIGS. 11a-11b schematically show a second embodiment of the particle redirector according to one aspect of the present disclosure.

FIGS. 11*a*-11*b* show a similar particle redirector 100' as in FIGS. 8*a*-8*d* with similar features except for the base 101 having a slightly different shape. Only the differences will be described. The base 101 still has a convex surface 102 and a concave surface 103 and a peripheral edge 104, however the base has a "saddle-shape". The general three-dimensional shape of the base 101 can be described as the shape defined by a surface of a hyperbolic paraboloid onto which a planar ellipse has been overlaid.

The disclosure also covers all conceivable combinations of the described aspects, variants, alternatives and example embodiments of the disclosure.

Furthermore, the disclosure is not limited to the aforesaid aspects or examples but is naturally applicable to other aspects and example embodiments within the scope of the following claims.

Reference signs mentioned in the claims should not be seen as limiting the extent of the matter protected by the claims, and their sole function is to make claims easier to understand.

The invention claimed is:

1. An apparatus for manufacturing an absorbent core for an absorbent product, said absorbent core comprises a fibrous material and particles dispersed throughout at least a portion of said fibrous material, said apparatus comprising:

a movable mat-forming device comprising at least one mould, said movable mat-forming device is movable in a machine direction, a passage for directing at least a mixture of said fibrous material and said particles towards said at least one mould for depositing at least one layer of said mixture of said fibrous material and said particles in said mould, a particle supply duct having an opening inside said passage, wherein said apparatus further comprises a particle redirector arranged adjacent to said opening of said particle supply duct and said particle redirector is pivotable in said machine direction or against said machine direction around a pivot axis extending in the cross direction to said machine direction and thereby redirecting said particles to at least one area on said at least one mould, wherein the particle redirector has a first surface and a second surface, wherein when the first surface is facing in an upward direction, the particles are directed to one end or another of said at least one mould, and when the second surface is facing in the upward direction, the particles are directed in one or more central areas of the at least one mould.

2. An apparatus for manufacturing an absorbent core for an absorbent product, said absorbent core comprises a fibrous material and particles dispersed throughout at least a portion of said fibrous material, said apparatus comprising:

a movable mat-forming device comprising at least one mould, said movable mat-forming device is movable in a machine direction, a passage for directing at least a mixture of said fibrous material and said particles towards said at least one mould for depositing at least one layer of said mixture of said fibrous material and said particles in said mould, a particle supply duct having an opening inside said passage, wherein said apparatus further comprises a particle redirector arranged adjacent to said opening of said particle supply duct and said particle redirector is pivotable in said machine direction or against said machine direction around a pivot axis extending in the cross direction to said machine direction and thereby redirecting said particles to at least one area on said at least one mould, wherein said particle redirector comprises a base which has convex surface and an opposite concave surface and a peripheral edge, a first imaginary plane is aligned along said pivot axis and bisects said base into two halves such that the cross section of said base taken along said first imaginary plane is U- or V-shaped;

a second imaginary plane is perpendicular to said first imaginary plane, and said first imaginary plane and said second imaginary plane intersect along said pivot axis PA;

a third imaginary plane bisects said base into two halves, said third imaginary plane is perpendicular to said first imaginary plane and said second imaginary plane, and said third imaginary plane intersects with said first imaginary plane along a first axis and intersects with said second said imaginary plane along a second axis;

said particle redirector comprises at least a first flange and a second flange extending from said convex surface on respective sides of said first imaginary plane, and essentially parallel with the first imaginary plane, wherein said concave surface or said convex surface together with said flanges direct said particles towards said mould, and said pivot axis is arranged at the centre of gravity of said particle redirector or at distance from said centre of gravity along said first imaginary plane.

3. An apparatus according to claim 2 wherein the first imaginary plane bisects said base into two equal halves and said third imaginary plane bisects said base into two equal halves.

4. An apparatus according to claim 1, wherein said particles are super absorbent particles, heat activatable bonding particles or odour absorbent particles.

5. An apparatus according to claim 2, wherein a third flange extends from said convex surface aligned and parallel with said first imaginary plane.

6. An apparatus according to claim 2, wherein a fourth flange extends from said convex surface aligned and parallel with said third imaginary plane between said first and said second flange.

7. An apparatus according to claim 2, wherein said pivot axis at a cross-section taken along said third imaginary plane is arranged at a substantially equal predetermined distance from a highest point of each said first, second and/or third flange and from an outer point of the peripheral edge (104) on each side of the first imaginary plane.

8. An apparatus according to claim 2, wherein said first, second and/or third flange each has a curved outer shape extending from a highest point of each respective flange towards said convex surface, viewed from the normal direction of said first imaginary plane.

9. An apparatus according to claim 2, wherein the particle redirector has an outer contour, formed by the first, second and/or third flanges together with the base, which follows the shape of an imaginary surface of a partially imaginary ellipsoid.

10. An apparatus according to claim 2, wherein at least a part of said particle redirector protrude into said opening of the particle supply duct or said particle redirector is arranged in close proximity to said opening of said particle supply duct.

11. An apparatus according to claim 2, wherein said opening of said particle supply duct has a shape and/or a diameter which allows the outer contour of said particle redirector to pivot freely adjacent or at least partly inside said particle supply duct.

12. An apparatus according to claim 2, wherein the first and the second flanges are arranged at a distance from each other which is equal, smaller or larger than the inner diameter opening of the particle supply duct.

13. An apparatus according to claim 2, wherein the maximum width of the base of the particle redirector at a cross section taken along said first imaginary plane is equal or larger than the inner diameter of the particle supply duct.

14. An apparatus according to claim 2, wherein said first axis of said particle redirector is aligned with a centre axis of said particle supply duct.

15. An apparatus according to claim 1, wherein said particle redirector comprises a shaft connecting element extending along said pivot axis adapted to house a shaft which is connectable to said shaft connecting element in order to pivot said particle redirector around said pivot axis.

16. An apparatus according to claim 1, wherein said particle redirector is pivotable around said pivot axis by a shaft connected to said particle redirector which is rotatable supported in said passage.

17. An apparatus according to claim 1, wherein said particle redirector is pivotable around said pivot axis by a motor.

18. A particle redirector comprising a base which has convex surface and an opposite concave surface and a peripheral edge, a first imaginary plane is aligned along a pivot axis and bisects said base into two halves such that a cross section of said base at said first imaginary plane is U or V shaped;

a second imaginary plane is perpendicular to said first imaginary plane, and said first imaginary plane and said second imaginary plane intersect along said pivot axis;

a third imaginary plane bisects said base into two halves, said third imaginary plane is perpendicular to said first imaginary plane and said second imaginary plane, and said third imaginary plane intersects with said first imaginary plane along a first axis and intersects with said second said imaginary plane along a second axis;

said particle redirector comprises at least a first flange and a second flange extending from said convex surface on respective sides of said first imaginary plane and essentially parallel with the first imaginary plane, and said pivot axis is arranged at the centre of gravity of said particle redirector or at distance from said centre of gravity along said first imaginary plane.

19. A particle redirector according to claim 18, wherein the first imaginary plane bisects said base into two equal halves and said third imaginary plane bisects said base into two equal halves.

20. A particle redirector according to claim 18, wherein a third flange extends from said convex surface aligned and parallel with said first imaginary plane.

21. A particle redirector according to claim 18, wherein a fourth flange extends from said convex surface aligned and parallel with said third imaginary plane between said first and said second flange.

22. A particle redirector according to claim 18, wherein said pivot axis at a cross-section taken along said third imaginary plane is arranged at a substantially equal predetermined distance from a highest point of each said first, second and/or third flange and from an outer point of the peripheral edge on each side of the first imaginary plane.

23. A particle redirector according to claim 18, wherein said first, second and/or third flange each has a curved outer shape extending from a highest point of each respective flange towards said convex surface, viewed from the normal direction of said first imaginary plane.

24. A particle redirector according to claim 18, wherein the particle redirector has an outer contour, formed by the first, second and/or third flanges together with the base, which follows the shape of an imaginary surface of a partially imaginary ellipsoid.

25. A particle redirector according to claim 18, wherein the first and the second flanges are arranged at a distance from each other.

26. A particle redirector according to claim 18, wherein the base of the particle redirector has a maximum width at the cross section taken along said first imaginary plane.

27. A particle redirector according to claim 18, wherein said particle redirector comprises a shaft connecting element extending along said pivot axis adapted to house a shaft which is connectable to said shaft connecting element in order to pivot said particle redirector around said pivot axis.

28. A method of redirecting particles supplied from an opening of a particle supply duct inside a passage which directs said particles towards at least one mould on a movable mat-forming device which is moving in a machine direction, said redirection is made with a particle redirector arranged adjacent to said opening and said particle redirector is pivotable around a pivot axis, which is extending in the cross direction to said machine direction of said movable mat-forming device, said method comprises the step pivoting said particle redirector around said pivot axis in the direction along and/or against said machine direction and thereby redirecting said particles to at least one area on said at least one mould, wherein the particle redirector has a first surface and a second surface, wherein when the first surface is facing in an upward direction, the particles are directed to one end or another of said at least one mould, and when the second surface is facing in the upward direction, the particles are directed in one or more central areas of the at least one mould.

29. A method of redirecting particles supplied from an opening of a particle supply duct inside a passage which directs said particles towards at least one mould on a movable mat-forming device which is moving in a machine direction, said redirection is made with a particle redirector arranged adjacent to said opening and said particle redirector is pivotable around a pivot axis, which is extending in the cross direction to said machine direction of said movable mat-forming device, said method comprises the step pivoting said particle redirector around said pivot axis in the direction along and/or against said machine direction and thereby redirecting said particles to at least one area on said at least one mould, wherein said particle redirector is a particle redirector according to claim 18.

30. A method according to claim 28, wherein said particle redirector is from a starting position in a first step pivoting at a first speed in the same direction the mat-forming device or in the opposite direction of the mat-forming device so that particles are directed to a certain area on said mould.

31. A method according to claim 30, wherein said particle redirector in a second step is pivoting in the opposite direction to said first direction at a second speed which is higher than the first speed.

* * * * *